(12) United States Patent
Virgili Bernado et al.

(10) Patent No.: US 9,926,276 B2
(45) Date of Patent: Mar. 27, 2018

(54) SUBSTITUTED BENZAMIDES WITH ACTIVITY TOWARDS EP4 RECEPTORS

(71) Applicant: DRACONIS PHARMA, S.L., Barcelona (ES)

(72) Inventors: Marina Virgili Bernado, Barcelona (ES); Elena Carceller Gonzalez, Barcelona (ES); Jordi Salas Solana, Barcelona (ES)

(73) Assignee: DRACONIS PHARMA, S.L., Barcelona (ES)

( * ) Notice: Subject to any disclaimer, the term of this patent is extended or adjusted under 35 U.S.C. 154(b) by 0 days.

(21) Appl. No.: 14/766,654

(22) PCT Filed: Feb. 7, 2014

(86) PCT No.: PCT/EP2014/052437
§ 371 (c)(1),
(2) Date: Aug. 7, 2015

(87) PCT Pub. No.: WO2014/122267
PCT Pub. Date: Aug. 14, 2014

(65) Prior Publication Data
US 2015/0376129 A1    Dec. 31, 2015

Related U.S. Application Data

(60) Provisional application No. 61/770,096, filed on Feb. 27, 2013.

(30) Foreign Application Priority Data

Feb. 7, 2013  (EP) ..................................... 13382037

(51) Int. Cl.
| | |
|---|---|
| *C07C 233/81* | (2006.01) |
| *C07C 235/42* | (2006.01) |
| *C07D 213/81* | (2006.01) |
| *C07C 255/57* | (2006.01) |
| *C07D 239/26* | (2006.01) |
| *C07C 235/56* | (2006.01) |

(52) U.S. Cl.
CPC .......... *C07D 213/81* (2013.01); *C07C 233/81* (2013.01); *C07C 235/42* (2013.01); *C07C 235/56* (2013.01); *C07C 255/57* (2013.01); *C07D 239/26* (2013.01); *C07C 2601/04* (2017.05); *C07C 2601/14* (2017.05)

(58) Field of Classification Search
None
See application file for complete search history.

(56) References Cited

U.S. PATENT DOCUMENTS 5,516,774 A * 5/1996 Albright .............. C07D 487/04
514/220

FOREIGN PATENT DOCUMENTS

| EP | 0636625 A2 | 2/1995 |
| EP | 2172447 A1 | 4/2010 |
| GB | 1418762 | * 1/1973 |
| WO | 2008071736 A1 | 6/2008 |
| WO | 2011102149 A1 | 8/2011 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
International Search Report and Written Opinion dated Apr. 1, 2014 in International Application No. PCT/EP2014/052437.
Database Registry [Online] Chemical Abstracts Service, Columbus, Ohio, US; Sep. 28, 2008 (Sep. 28, 2008), XP002695840, retrieved from STN Database accession No. 1053913-35-1.
Database Registry [Online] Chemical Abstracts Service, Columbus, Ohio, US; Apr. 23, 2008 (Apr. 23, 2008), XP002695841, retrieved from STN Database accession No. 1016672-94-8.
Database Registry [Online] Chemical Abstracts Service, Columbus, Ohio, US; Sep. 18, 2008 (Sep. 18, 2008), XP002695842, retrieved from STN Database accession No. 1050194-09-6.
Database Registry [Online] Chemical Abstracts Service, Columbus, Ohio, US; May 1, 2012 (May 1, 2012), XP002695843, retrieved from STN Database accession No. 1371722-98-3.
Database Registry [Online] Chemical Abstracts Service, Columbus, Ohio, US; Apr. 29, 2012 (Apr. 29, 2012), XP002695844, retrieved from STN Database accession No. 1371040-11-7.
Database Registry [Online] Chemical Abstracts Service, Columbus, Ohio, US; May 22, 2011 (May 22, 2011), XP002695846, retrieved from STN Database accession No. 1298410-18-0.
European Search Report May 13, 2013 in European Application No. 13382037.3.
Database Registry [Online] Chemical Abstracts Service, Columbus, Ohio, US; Aug. 24, 2011 (Aug. 24, 2011), XP002695845, retrieved from STN Database accession No. 1322501-85-8.
Database Registry [Online] Chemical Abstracts Service, Columbus, Ohio, US; Aug. 14, 2011 (Aug. 14, 2011), XP002695847, retrieved from STN Database accession No. 1317490-41-7.
Database Registry [Online] Chemical Abstracts Service, Columbus, Ohio, US; Feb. 8, 2012 (Feb. 8, 2012), XP002695848, retrieved from STN Database accession No. 1355926-80-5.
Chen et al., A Novel Antagonist of the Prostaglandin E2 EP4 Receptor Inhibits Th1 Differentiation and Th17 Expansion and is Orally Active in Arthritis Models, Research Paper, British Journal of Pharmacology (2010), 160, 292-310, Andover, MA.
Cherukuri et al., The EP4 Receptor Antagonist, L-161,982, Blocks Prostaglandin E2-induced Signal Transduction and Cell Proliferation in HCA-7 Colon Cancer Cells, Author Manuscript, NIH Public Access, Exp Cell Res. (Aug. 15, 2007) 313(14): 2969-2979. doi:10.1016/j.yexcr.2007.06.004, Tucson, AZ.

(Continued)

*Primary Examiner* — Sudhakar Katakam
*Assistant Examiner* — Jennifer C Sawyer
(74) *Attorney, Agent, or Firm* — Polsinelli PC

(57) ABSTRACT

The present invention belongs to the field of EP4 receptor ligands. More specifically it refers to compounds of general formula (I) having great affinity and selectivity for the EP4 receptor. The invention also refers to the process for their preparation, to their use as medicament for the treatment and/or prophylaxis of diseases or disorders mediated by the EP4 receptor as well as to pharmaceutical compositions comprising them.

18 Claims, No Drawings

(56) References Cited

OTHER PUBLICATIONS

Chuang et al., Mechanisms and Urodynamic Effects of a Potent and Selective EP4 Receptor Antagonist, MF191, on Cyclophosphamide and Prostaglandin E 2-induced Bladder Overactivity in Rats, BJU International (Dec. 20, 2011) 110, 1558-1564, Pittsburgh, PA, USA.
Dirig et al., In Vitro Prostanoid Release from Spinal Cord Following Peripheral Inflammation: Effects of Substance P, NMDA and Capsaicin, British Journal of Pharmacology (1999) 126, 1333-1340, La Jolla, CA, USA.
Davis et al., EP4 Prostanoid Receptor-Mediated Vasodilatation of Human Middle Cerebral Arteries, British Journal of Pharmacology (2004) 141, 580-585, Babraham, Cambridge.
Judah Folkma, Angiogenesis: An Organizing Principle for Drug Discovery?, Nature Reviews|Drug Discovery (Apr. 2007) Nature Publishing Group, vol. 6, 273.
Fujino et al., Prostaglandin E2 Induced Functional Expression of Early Growth Response Factor-1 by EP4, but Not EP2, Prostanoid Receptors via the Phosphatidylinositol 3-Kinase and Extracellular Signal-regulated Kinases, The Journal of Biological Chemistry, The American Society for Biochemistry and Molecular Biology, Inc. (Apr. 4, 2003) vol. 278, No. 14, pp. 12151-12156, Tucson, AZ.
Guay et al., Carrageenan-induced Paw Edema in Rat Elicits a Predominant Prostaglandin E2 (PGE2) Response in the Central Nervous System Associated with the Induction of Microsomal PGE2 Synthase-1, The Journal of Biological Chemistry, The American Society for Biochemistry and Molecular Biology, Inc. (Jun. 4, 2004) vol. 279, No. 23, pp. 24866-24872, Canada.
Heidenreich et al., Angiogenesis Drives Psoriasis Pathogenesis, Review Article, Int. J. Exp. Path. (2009) 90, 232-248, Tubingen, Germany.
Jones et al., Prostanoid Receptor Antagonists: Development Strategies and Therapeutic Applications, Themed Issue: GPCR Review, British Journal of Pharmacology (2009) 158, 104-145, Irvine, CA, USA.
Lee et al., Selective Blockade of Prostaglandin E2 Receptors EP2 and EP4 Signaling Inhibits Proliferation of Human Endometriotic Epithelial Cells and Stromal Cells through Distinct Cell Cycle Arrest, American Society for Reproductive Medicine, Published by Elsevier Inc., Fertility and Sterility, vol. 93, No. 8, May 15, 2010.
Lin et al., Prostaglandin E2 Receptor EP4 Contributes to Inflammatory Pain Hypersensitivity, The Journal of Pharmacology and Experimental Therapeutics, The American Society for Pharmacology and Experimental Therapeutics, Sep. 7, 2006, USA.
Ma et al., Morphological and Pharmacological Evidence for the Role of Peripheral Prostaglandins in the Pathogenesis of Neuropathic Pain, Federation of European Neuroscience Societies, European Journal of Neuroscience, vol. 15, pp. 1037-1047 (Feb. 5, 2002) Winston-Salem, North Carolina, USA.
Maher, Prostanoids and the Cough Reflex, Springer Science+Business Media, LLC (Oct. 15, 2009) Lung (2010) 188(Suppl 1):S9-S12, DOI 10.1007/s00408-009-9190-2, London, UK.
Maubach et al., BGC20-1531, a novel, potent and selective prostanoid EP4 receptor antagonist: a putative new treatment for migraine headache, Research Paper, British Journal of Pharmacology (2009), 156, 316-327, UK.
McCoy et al., The Role of Prostaglandin E2 Receptors in the Pathogenesis of Rheumatoid Arthritis, J. Clin. Invest. 110:651-658 (2002). doi:10.1172/JCI200215528, Pfizer Global Research and Development, Department of Inflammation and Pathology, Groton, Connecticut, USA.
Narumiya et al., Prostanoid Receptors: Structures, Properties, and Functions, Physiological Reviews, vol. 79, No. 4 (Oct. 1999) American Physiological Society, USA.
Oka et al., Biphasic Modulation in the Trigeminal Nociceptive Neuronal Responses by the Intracerebroventricular Prostaglandin E may be Mediated through Different 2 EP Receptors Subtypes in Rats, Research Report, Elsevier Science B.V., Brain Research 771 (1997) 278-284.
Coleman et al., VIII. International Union of Pharmacology Classification of Prostanoid Receptors: Properties, Distribution, and Structure of the Receptors and their Subtypes, Pharmacology Reviews, The American Society for Pharmacology and Experimental Therapeutics, vol. 46, No. 2 (Jun. 1994) USA.
Samad et al., Prostanoids and Pain: Unraveling Mechanisms and Revealing Therapeutic Targets, Review, Trends in Molecular Medicine, vol. 8, No. 8, Elsevier Science Ltd. (Aug. 2002) USA.
Syriatowicz et al., Hyperalgesia Due to Nerve Injury: Role of Prostaglandins, Pergamon, Neuroscience, vol. 94, No. 2, pp. 587-594, Elsevier Science Ltd (1999) Great Britain.
Takayama et al., Novel Prostaglandin E Receptor 4-Associated Protein Participates in Antiinflammatory Signaling, Circulation Research (Mar. 3, 2006) DOI: 10.1161/01.RES.0000204451.88147. 96, Boston, MA.
Wei et al., Roles of the Prostaglandin E2 Receptors EP Subtypes in Alzheimer's Disease, Neurosci Bull, 26(1): 77-84, DOI: 10.1007/s12264-010-0703-z, Shanghai Institutes for Biological Sciences, CAS and Springer-Verlag, Berlin Heidelberg, Feb. 1, 2010.
Wu et al., EP4 Upregulation of Ras Signaling and Feedback Regulation of Ras in Human Colon Tissues and Cancer Cells, Genotoxicity and Carcinogenicity, Arch Toxicol (2010) 84:731-740, DOI 10.1007/s00204-010-0562-4, Springer-Verlag, Berlin Heidelberg, Jun. 23, 2010.
Yao et al., Prostaglandin E2-EP4 Signaling Promotes Immune Inflammation through TH1 Cell Differentiation and TH17 Cell Expansion, Articles, Nature Medicine, vol. 15, No. 6, Nature America, Inc., Jun. 2009.
Yao et al., Prostaglandin E2 Promotes Th1 Differentiation via Synergistic Amplification of IL-12 Signalling by cAMP and PI3-kinase, Nature Communications | 4:1685 | DOI: 10.1038/ncomms2684, Macmillan Publishers Limited (Apr. 9, 2013), UK.
Michal Zimecki, Potential Therapeutic Interventions via EP2/EP4 Prostaglandin Receptors, Postepy Hig Med Dosw, Review (2012) 66: 287-294, Department of Experimental Therapy, The Institute of Immunology and Experimental Therapy, Wroclaw, Poland.

* cited by examiner

SUBSTITUTED BENZAMIDES WITH ACTIVITY TOWARDS EP4 RECEPTORS

CROSS-REFERENCE TO RELATED APPLICATIONS

The present application is a national stage entry of international application number PCT/EP2014/052437, which was filed on Feb. 7, 2014 which claims priority to European Application 13382037.3, which was filed Feb. 7, 2013 and benefit of U.S. Application 61/770,096, which was filed on, Feb. 27, 2013, each of the applications are hereby incorporated by reference in their entireties.

FIELD OF THE INVENTION

The present invention belongs to the field of EP4 receptor ligands. More specifically it refers to compounds of general formula (I) having great affinity and selectivity for the EP4 receptor. The invention also refers to the process for their preparation, to their use as medicament for the treatment and/or prophylaxis of diseases or disorders mediated by the EP4 receptor as well as to pharmaceutical compositions comprising them.

BACKGROUND OF THE INVENTION

Prostanoids are a family of eicosanoids that comprise prostaglandins (PGs), prostacyclins (PGIs), and thromboxanes (Txs). Their receptors belong to the G-protein coupled receptor (GPCR) superfamily of receptors and may be grouped into five classes, namely, prostaglandin D (DP), prostaglandin E (EP), prostaglandin F (FP), prostaglandin I (IP), and Thromboxane A (TP) based on their sensitivity to five naturally occurring prostanoids, PGD2, PGE2, PGF2[alpha], PGI2, and TxA2, respectively (Coleman, R. A., 2000).

Prostaglandins are small potent inflammatory mediators that are generated by the release of arachidonic acid (AA) from the membrane phospholipids. Subsequently, cyclooxigenase and prostaglandin synthase enzymes metabolize AA to prostaglandins that play pivotal roles in the modulation of physiological systems, such as CNS, and the inflammatory and immune responses.

Prostaglandins contribute to the sensitization of peripheral and central nociceptive neurons during peripheral inflammation (Dirig and Yaksh, 1999) and play an important role in the pathogenesis of neuropathic pain following nerve injury (Syriatowicz et al 1999; Samad et al, 2002; Ma and Eisenach, 2003).

Prostaglandin E2 (PGE2) is considered to be the dominant pro-nociceptive prostanoid. Guay and colleagues, analyzing the concentrations of different prostaglandins in the cerebrospinal fluid, found that PGE2 was the most prevalent prostanoid and exhibited the highest increase after peripheral carrageenan-induced inflammation (Guay et al., 2004). PGE2 is generated in most cells in response to mechanical, thermal or chemical injury and inflammatory insult, resulting in sensitization or direct activation of nearby sensory nerve endings. Its production requires the activity of at least one of the two cyclooxygenase isoforms, COX-1 constitutively expressed or COX-2 which is inducible and particularly relevant for inflammation-induced PGE2 formation. Therefore, non-selective inhibitors of COX-1 and COX-2, and selective COX-2 inhibitors provide good pain relief. However, the long-term use is associated with gastrointestinal or cardiovascular side effects, respectively.

Downstream components of the inflammatory cascade could be an alternative approach for the treatment of the PGE2 associated pain. PGE2 binds to four different G-protein coupled receptors named EP1, EP2, EP3 and EP4 (Narumiya et al., 1999).

Studies employing antagonists suggest that blocking EP1, EP2, EP3 or EP4 receptors may reduce certain types of pain (Oka et al. 1997; Lin et al, 2006). Among these PGE2 receptors, most of the drug discovery studies have focused on modulating EP4 receptor. EP4 receptor has been associated in various models of immune response, inflammation, hypoxia, organ damage, autoimmunity, bone catabolism and transplantation (M. Zimecki, 2012), revealing therapeutic utility of application of either agonist or antagonist of EP4 receptor.

EP4 receptor couples mainly to Gs and mediates transient increase in intracellular cAMP concentration. In turn, cAMP activates protein kinase A (PKA), which then phosphorilates downstream effector proteins, in particular cAMP response element-binding protein (CREB). Furthermore, an EP4 receptor-associated protein (EPRAP) which binds to the unique long carboxyl terminal cytoplasmatic domain of EP4 receptor has been described to participate in anti-inflammatory signalling (Takayama, K. et al. 2006). In addition, EP4 receptors activate the phosphatidylinositol 3-kinase (PI3K) signalling pathway (Fujino et al., 2003).

Rheumatoid arthritis (RA) is a chronic inflammatory disorder leading to bone and cartilage destruction. A substantial body of evidence suggests that prostaglandin E2 (PGE2) contributes to the pathogenesis of RA, and non-steroidal anti-inflammatory drugs, inhibitors of the synthesis of PGE2 and other prostanoids, continue to be used in the treatment of this disease.

McCoy and colleagues examined mice lacking each of the four known PGE2 (EP) receptors after generation of collagen antibody-induced arthritis, an animal model of RA. Homozygous deletion of the EP1, EP2, or EP3 receptors did not affect the development of arthritis, whereas EP4 receptor-deficient mice showed decreased incidence and severity of disease. These animals also showed reduced inflammation as assessed by circulating IL-6 and serum amyloid A levels. Joint histopathology of EP4−/− animals revealed reduced bone destruction, proteoglycan loss, and type II collagen breakdown in cartilage compared with EP4+/+ mice. Furthermore, liver and macrophages isolated from EP4−/− animals produced significantly less IL-1β and IL-6 than control samples. Thus, PGE2 contributes to disease progression at least in part by binding to the EP4 receptor. Antagonists of this receptor might therefore provide novel agents for the treatment of RA. (McCoy et al. 2002)

Recent studies involving parenteral administration of several EP4 antagonists (AH-23848, CJ-023423, CJ-042794, MF-498, ONO-AE3-208) have clearly demonstrated a major involvement of EP4 receptors in small-animal models of inflammation. Joint pain, mechanical and thermal hyperalgesia and edema were markedly suppressed, often equivalent to the efficacy of selective COX-2 inhibitors such as rofecoxib. (Jones et al, 2009). These are more evidences that EP4 antagonists might provide novel agents for the treatment of rheumatoid arthritis and osteoarthritis.

Two distinct helper T (TH) subsets, TH1 and TH17, mediate tissue damage and inflammation in animal models of various immune diseases such as multiple sclerosis, rheumatoid arthritis, inflammatory bowel diseases, psoriasis and other allergic skin disorders. These experimental findings, and the implication of these TH subsets in human diseases, suggest the need for pharmacological measures to manipulate these TH subsets. Yao C. and colleagues showed that prostaglandin E2 (PGE2) acting on its receptor EP4 on T cells and dendritic cells not only facilitates TH1 cell differentiation but also amplifies interleukin-23-mediated TH17 cell expansion in vitro. Administration of an EP4-selective antagonist in vivo decreases accumulation of both TH1 and TH17 cells in regional lymph nodes and suppresses the disease progression in mice subjected to experimental autoimmune encephalomyelitis, contact hypersensitivity or colitis model (Yao C., 2009 and 2013) and different remathoid arthritis models (Chen Q., et al. 2010). Thus, PGE2-EP4 signaling promotes immune inflammation through TH1 differentiation and TH17 expansion, and EP4 antagonism is proposed as a promising drug target for immunomodulation and may be therapeutically useful for various immune diseases (Yao C. et al. 2009).

Significant cross-talk can occur between the cannonical signalling pathways described above and several additional pathways can be activated in some cells. One of the most important of these is the recent demonstration that the EP1, EP2 and EP4 receptors can transactivate the epidermal growth factor receptor (EGFR) which is implicated in proliferation, invasion, resistance to apoptosis, angiogenesis, and metastasis, all of which are associated with tumor development (Wu, W. et al. 2010). Angiogenesis is also closely linked with clinical manifestations of non-noplastic diseases such as some autoimmune diseases (e.g. psoriasis, reumathoid arthritis, . . . ), age-related macular degeneration and atherosclerosis (Folkman J., 2007, Heidenreich R., 2009).

Accumulating evidence indicates that elevated levels of prostaglandin E2 (PGE2) can increase intestinal epithelial cell proliferation, and thus play a role in colorectal tumorigenesis. PGE2 exerts its effects through four G-protein-coupled PGE receptor (EP) subtypes, named the EP1, EP2, EP3, and EP4. Increased phosphorylation of extracellular regulated kinases (ERK1/2) is required for PGE2 to stimulate cell proliferation of human colon cancer cells. Cherukuri and colleagues provide evidence that L-161,982, a selective EP4 receptor antagonist, completely blocks PGE2-induced ERK phosphorylation and cell proliferation of HCA-7 cells. They concluded that egr-1 is a target gene of PGE2 in HCA-7 cells and is regulated via the newly identified EP4/ERK/CREB pathway (Cherukuri et al., 2007). These results support the notion that antagonizing EP4 receptors may provide a novel therapeutic approach to the treatment of colon cancer.

EP4 receptor antagonists may have therapeutic utility in the treatment of migraine since it has been observed that EP4 antagonists block $PGE_2$-induced relaxation of human-isolated middle cerebral artery (Davis et al., 2004; Maubach et al., 2009) and the picture has been enlarged to include the interaction of endogenous $PGE_2$ with calcitonin gene-related peptide release from trigeminal nerves (Maubach et al., 2009).

Chuang and colleagues found that MF191, a selective EP4 receptor antagonist, may have effects on the bladder urothelium and inflammatory cells and suppress CYP- or PGE 2-induced bladder overactivity (Chuang et al, 2012). EP4 receptor antagonists may be useful for the treatment of overactive bladder.

Additional therapeutic applications for EP4 antagonists are modulation of the cough reflex (Maher et al 2010), treatment for endometriosis in women (Lee et al 2010) and Alzheimer's disease (Wei et al, 2010).

Based on the above mentioned results coming from animal and human studies, EP4 receptor has been identified as a selective target for the development of new potential therapies for the treatment of those disorders where PGE2 action is involved. In view of the potential therapeutic applications of agonists and antagonists of the EP4 receptor, a great effort is being directed to find selective ligands. Despite intense research efforts in this area, very few compounds with selective EP4 activity have been reported.

There is thus still a need to find compounds having pharmacological activity towards the EP4 receptor, being both effective and selective, having good "druggability" properties, i.e. good pharmaceutical properties related to administration, distribution, metabolism and excretion and showing a good toxicological profile.

The present invention hereby provide some novel compounds complying with the above mentioned properties.

OBJECT OF THE INVENTION

The present invention discloses novel compounds with great affinity to EP4 receptors which might be used for the treatment of EP4-related disorders or diseases.

Specifically, it is an object of the invention a compound of general formula (I):

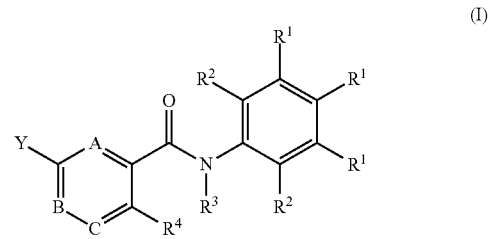

wherein:
each $R^1$ may be a —COOH a H; a halogen; a tetrazol; a —$SO_2$—NH—C(=O)—R'; a —C(=O)NH—$SO_2$—R'; or a —$SO_2$—OH with the proviso that only one of them must always represent a —COOH or tetrazol or —$SO_2$—NH—C(=O)—R' or —C(=O)NH—$SO_2$—R' or —$SO_2$—OH, each $R^2$ is independently selected from the group consisting of H; a halogen; $C_{1-6}$-alkyl; or —O—$C_{1-6}$-alkyl, with the proviso that at least one $R^2$ must be different from H $R^3$ is selected from H; or a $C_{1-6}$-alkyl;
$R^4$ is a halogen or a $C_{1-6}$-alkyl;
A, B and C independently represents a $CR^a$ or a N;
Y is a —$NR^5R^6$; an —$OR^7$; a phenyl, optionally substituted by at least one $R^b$; a benzyl optionally substituted by at least one $R^b$; a 5- or 6-membered heterocyclic ring, optionally substituted by at least one $R^b$, containing at least one heteroatom selected from N, O or S; a $C_{1-4}$-alkylene-$C_{3-6}$-cycloalkyl; or a $C_{1-6}$-alkyl;
$R^5$ and $R^6$ are independently selected from H; a $C_{1-6}$-alkyl; a benzyl; a $C_{3-6}$cycloalkyl; —$C_{1-4}$-alkylene-$C_{3-6}$cycloalkyl; or —$C_{1-4}$-alkylene-$C_{1-6}$-alkyloxy;

$R^7$ is a H, a $C_{1-6}$-alkyl, a benzyl optionally substituted by at least one $R^c$; or a —$C_{1-4}$-alkylene-$C_{3-6}$cycloalkyl;

R' is independently selected from a hydrogen; $C_{1-6}$-alkyl; an optionally substituted phenyl; or —$N(CH_3)_2$;

$R^a$ is a H or a $C_{1-6}$-alkyl;

each $R^b$ is independently a H; a $C_{1-6}$-alkyl; a halogen; a —CN; a trihalo-$C_{1-6}$-alkyl; a —$CONR^8R^9$; an —$OR^{10}$ or —$C_{1-4}$-alkylene-$OR^{11}$;

each $R^c$ is independently a H; a $C_{1-6}$-alkyl; or a halogen;

$R^8$ and $R^9$ are independently selected from H; or a $C_{1-6}$-alkyl;

$R^{10}$ and $R^{11}$ are independently selected from H; or a $C_{1-6}$-alkyl;

with the proviso that when $R^1$ is COOH in meta position and $R^2$ is either methyl or Cl or when $R^1$ is COOH in para position and $R^2$ is methyl, $R^7$ is not methyl and $R^4$ is not Br and the salts, solvates and prodrugs thereof.

It is also an object of the invention the process for the preparation of compounds of general formula (I).

In another aspect, the invention relates to a compound of general formula (I) for use as a medicament.

Yet another object of the invention is a compound of general formula (I) for use in the treatment and/or prophylaxis of diseases or disorders mediated by the EP4 receptor. This includes but is not limited to diseases such as inflammatory related pain including low back and neck pain, skeletal pain, post-partum pain, toothache, sprains and straits, myositis, neuralgia, synovitis, arthritis, including rheumatoid arthritis, degenerative joint diseases, gout and ankylosing spondylitis, bursitis, burns including radiation and corrosive chemical injuries and sunburns; postoperative pain; neuropathic pain; visceral pain; tension headache; cluster headaches; migraine; motility-related disorders including gastrointestinal disorders, urinary incontinence and other urinary tract diseases; dysmenorrhea; preterm labour; diabetic retinopathy; tumour angiogenesis; cancer; metastatic tumour growth; neurodegenerative diseases including senile dementia, Alzheimer's disease, Pick's disease, Huntington's chorea, Parkinson's disease, Creutzfeldt-Jakob disease, or amyotrophic lateral sclerosis; neuroprotection/stroke; glaucoma; osteoporosis; bone fractures; Paget's disease; hyperthermia including different types of fever as rheumatic fever; symptoms associated with influenza or other viral infections; gastrointestinal disorders related with chemotherapy or irritable bowel syndrome; gastrointestinal bleeding; coagulation disorders including anaemia, hypoprothrombinemia, haemophilia or other bleeding problems; kidney diseases including nephritis, particularly mesangial proliferative glomerulonephritis and nephritic syndrome; thrombosis and occlusive vascular diseases; inflammatory diseases including the treatment of skin conditions such as sunburn, burns, eczema, dermatitis, psoriasis; ophthalmic diseases including glaucoma, retinitis, retinopathies, uveitis and of acute injury to the eye tissue such as conjunctivitis; lung disorders including asthma, bronchitis, emphysema, allergic rhinitis, respiratory distress syndrome pigeon fancier's disease, farmers lung, CORD; gastrointestinal tract disorders including aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease; organ tnasplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome; bone diseases characterized by abnormal bone metabolism or resorption such as osteoporosis, especially postmenopausal osteoporosis, hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis, especially urolithiasis, solid carcinoma, gout and ankylosing spondylitis, tendinitis and bursitis; immune diseases such as multiple sclerosis, rheumatoid arthritis, inflammatory bowel diseases and allergic skin disorders; contact hypersensitivity, cough and endometriosis.

It is another object of the invention a pharmaceutical composition comprising at least one compound of general formula (I) and at least one pharmaceutically acceptable carrier, additive, adjuvant or vehicle.

DETAILED DESCRIPTION OF THE INVENTION

In a first aspect the invention relates to compounds of general formula (I):

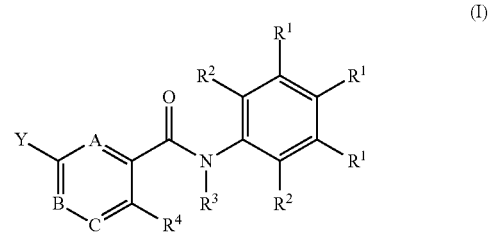

wherein:

each $R^1$ may be a —COOH a H; a halogen; a tetrazol; a —$SO_2$—NH—C(═O)—R'; a —C(═O)NH—$SO_2$—R'; or a —$SO_2$—OH with the proviso that only one of them must always represent a —COOH or tetrazol or —$SO_2$—NH—C(═O)—R' or —C(═O)NH—$SO_2$—R' or —$SO_2$—OH, each $R^2$ is independently selected from the group consisting of H; a halogen; $C_{1-6}$-alkyl; or —O—$C_{1-6}$-alkyl, with the proviso that at least one $R^2$ must be different from H $R^3$ is selected from H; or a $C_{1-6}$-alkyl;

$R^4$ is a halogen or a $C_{1-6}$-alkyl;

A, B and C independently represents a $CR^a$ or a N;

Y is a —$NR^5R^6$; an —$OR^7$; a phenyl, optionally substituted by at least one $R^b$; a benzyl optionally substituted by at least one $R^b$; a 5- or 6-membered heterocyclic ring, optionally substituted by at least one $R^b$, containing at least one heteroatom selected from N, O or S; a $C_{1-4}$-alkylene-$C_{3-6}$-cycloalkyl; or a $C_{1-6}$-alkyl;

$R^5$ and $R^6$ are independently selected from H; a $C_{1-6}$-alkyl; a benzyl; a $C_{3-6}$cycloalkyl; —$C_{1-4}$-alkylene-$C_{3-6}$cycloalkyl; or —$C_{1-4}$-alkylene-$C_{1-6}$-alkyloxy;

$R^7$ is a H, a $C_{1-6}$-alkyl, a benzyl optionally substituted by at least one $R^c$; or a —$C_{1-4}$-alkylene-$C_{3-6}$cycloalkyl;

R' is independently selected from a hydrogen; $C_{1-6}$-alkyl; an optionally substituted phenyl; or —$N(CH_3)_2$;

$R^a$ is a H or a $C_{1-6}$-alkyl;

each $R^b$ is independently a H; a $C_{1-6}$-alkyl; a halogen; a —CN; a trihalo-$C_{1-6}$-alkyl; a —CONR$^8$R$^9$; an —OR$^{10}$ or —$C_{1-4}$-alkylene-OR$^{11}$;

each $R^c$ is independently a H; a $C_{1-6}$-alkyl; or a halogen;

$R^8$ and $R^9$ are independently selected from H; or a $C_{1-6}$-alkyl;

$R^{10}$ and $R^{11}$ are independently selected from H; or a $C_{1-6}$-alkyl;

with the proviso that when $R^1$ is COOH in meta position and $R^2$ is either methyl or Cl or when $R^1$ is COOH in para position and $R^2$ is methyl, $R^7$ is not methyl and $R^4$ is not Br and the salts, solvates and prodrugs thereof.

More particularly, the first aspect of the invention refers to compounds of general formula (I):

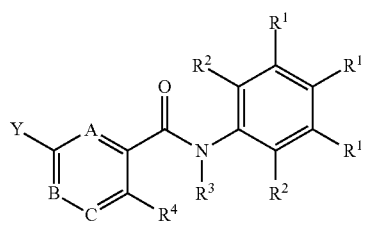

(I)

wherein:

each $R^1$ may be a —COOH a H; a halogen; a tetrazol; a —SO$_2$—NH—C(=O)—R'; a —C(=O)NH—SO$_2$—R'; or a —SO$_2$—OH with the proviso that only one of them must always represent a —COOH or tetrazol or —SO$_2$—NH—C(=O)—R' or —C(=O)NH—SO$_2$—R' or —SO$_2$—OH, each $R^2$ is independently selected from the group consisting of H; a halogen; $C_{1-6}$-alkyl; or —O—$C_{1-6}$-alkyl, with the proviso that at least one $R^2$ must be different from H $R^3$ is selected from H; or a $C_{1-6}$-alkyl;

$R^4$ is a halogen or a $C_{1-6}$-alkyl;

A, B and C independently represents a CR$^a$ or a N;

Y is a —NR$^5$R$^6$; an —OR$^7$; a phenyl, optionally substituted by at least one R$^b$; a benzyl optionally substituted by at least one R$^b$; a 5- or 6-membered heterocyclic ring, optionally substituted by at least one R$^b$, containing at least one heteroatom selected from N, O or S; a $C_{1-4}$-alkylene-$C_{3-6}$-cycloalkyl; or a $C_{2-6}$-alkyl;

$R^5$ and $R^6$ are independently selected from H; a $C_{1-6}$-alkyl; a benzyl; a $C_{3-6}$cycloalkyl; —$C_{1-4}$-alkylene-$C_{3-6}$cycloalkyl; or —$C_{1-4}$-alkylene-$C_{1-6}$-alkyloxy;

$R^7$ is a H, a $C_{1-6}$-alkyl, a benzyl optionally substituted by at least one R$^c$; or a —$C_{1-4}$-alkylene-$C_{3-6}$cycloalkyl;

R' is independently selected from a hydrogen; $C_{1-6}$-alkyl; an optionally substituted phenyl; or —N(CH$_3$)$_2$;

$R^a$ is a H or a $C_{1-6}$-alkyl;

each $R^b$ is independently a H; a $C_{1-6}$-alkyl; a halogen; a —CN; a trihalo-$C_{1-6}$-alkyl; a —CONR$^8$R$^9$; an —OR$^{10}$ or —$C_{1-4}$-alkylene-OR$^{11}$;

each $R^c$ is independently a H; a $C_{1-6}$-alkyl; or a halogen;

$R^8$ and $R^9$ are independently selected from H; or a $C_{1-6}$-alkyl;

$R^{10}$ and $R^{11}$ are independently selected from H; or a $C_{1-6}$-alkyl;

with the proviso that when $R^1$ is COOH in meta position and $R^2$ is either methyl or Cl or when $R^1$ is COOH in para position and $R^2$ is methyl, $R^7$ is not methyl and $R^4$ is not Br, and with the proviso that when $R^1$ is a is a tetrazol the circumstance where Y is methoxy or pirrolidinyl and $R^4$ is Br or Cl is not possible, and the salts, solvates and prodrugs thereof.

In a particular embodiment of the invention in the compounds of formula (I) when $R^1$ is COOH both $R^2$ are methyl, $R^4$ is methyl and Y is a piperidine substituted by and $R_b$, then $R_b$ does not represent an OR$^{10}$ with R$^{10}$ being a hydrogen.

Another particular embodiment of the invention is represented by compounds of formula (I) where Y a 5- or 6-membered heterocyclic ring, optionally substituted by at least one R$^b$. In this embodiment, the 5- or 6-membered heterocyclic ring is not a piperidine or pyrrolidine.

Also included within the scope of the invention are the isomers, polymorphs, isotopes, salts, solvates and prodrugs of the compounds of formula (I). Any reference to a compound of formula (I) throughout the present specification includes a reference to any isomer, polymorph, isotope, salt, solvate or prodrug of such compound of formula (I).

The compounds of formula (I) may exist in different physical forms, i.e. amorphous and crystalline forms. Moreover, the compounds of the invention may have the ability to crystallize in more than one form, a characteristic which is known as polymorphism. Polymorphs can be distinguished by various physical properties well known in the art such as X-ray diffraction pattern, melting point or solubility. All physical forms of the compounds of formula (I), including all polymorphic forms ("polymorphs") thereof, are included within the scope of the invention.

Some of the compounds of the present invention may exist as several optical isomers and/or several diastereoisomers. Diastereoisomers can be separated by conventional techniques such as chromatography or fractional crystallization. Optical isomers can be resolved by conventional techniques of optical resolution to give optically pure isomers. This resolution can be carried out on any chiral synthetic intermediate or on the products of formula I. Optically pure isomers can also be individually obtained using enantiospecific synthesis. The present invention covers all individual isomers as well as mixtures thereof (for example racemic mixtures or mixtures of diastereomers), whether obtained by synthesis or by physically mixing them.

In addition, any formula given herein is intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{36}$S, $^{18}$F, $^{36}$Cl, and $^{125}$I, respectively, Such isotopically labelled compounds are useful in metabolic studies (preferably with 14C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. In addition to the unlabeled form, all isotopically labeled forms of the compounds of formula I are included within the scope of the invention.

"Halogen" or "halo" as referred in the present invention represent fluorine, chlorine, bromine or iodine.

The term "alkyl," alone or in combination, means an acyclic radical, linear or branched, preferably containing from 1 to about 6 carbon atoms. Examples of such radicals include methyl, ethyl, n-propyl, isopropyl, n-butyl, isobutyl, sec-butyl, tert-butyl, pentyl, iso-amyl, hexyl, heptyl, octyl, and the like. Where no specific substitution is specified, alkyl radicals may be optionally substituted with groups consisting of hydroxy, sulfhydryl, methoxy, ethoxy, amino, cyano, chloro, and fluoro. The carbon atom content of various hydrocarbon-containing moieties is indicated by suffix designating a lower and upper number of carbon atoms in the moiety. Thus, for example, '$C_{1-6}$-alkyl' refers to alkyl of 1 to 6 carbon atoms, inclusive.

An "alkylene" linking group preferably contains 1-4 carbon atoms and represents for example methylene, ethylene, propylene, butylene. The carbon atom content of various hydrocarbon-containing moieties is indicated by suffix designating a lower and upper number of carbon atoms in the moiety. Thus, for example, '$C_{1-4}$-alkylene' refers to an alkylene of 1 to 4 carbon atoms, inclusive.

An "alkenylene" linking group preferably contains 2 to 4 carbon atoms and represents for example ethenylene, 1,3-propenylene, 1,4-but-1-enylene, 1,4-but-2-ethylene. The carbon atom content of various hydrocarbon-containing moieties is indicated by suffix designating a lower and upper number of carbon atoms in the moiety. Thus, for example, '$C_{2-4}$-alkenylene' refers to alkenylene of 2 to 4 carbon atoms, inclusive.

"Cycloalkyl" is preferably a monocyclic cycloalkyl containing from three to six carbon atoms. Examples include cyclopropyl, cyclobutyl, cyclopentyl, and cyclohexyl. The carbon atom content of various hydrocarbon-containing moieties is indicated by suffix designating a lower and upper number of carbon atoms in the moiety. Thus, for example, '$C_{3-6}$-cycloalkyl' refers to cycloalkyl of 3 to 6 carbon atoms, inclusive.

The term "carbocyclic", "carbocyclic ring" and "carbocyclyl" refer to a saturated, unsaturated or aromatic mono- or multi-ring cycloalkyl only formed from carbon atoms.

The terms "heterocycle", "heterocyclic ring" and "heterocyclyl" refer to a saturated, unsaturated or aromatic mono- or multi-ring cycloalkyl wherein one or more carbon atoms is replaced by N, S, or O. The terms "heterocycle", "heterocyclic ring system," and "heterocyclyl" include fully saturated ring structures such as piperazinyl, dioxanyl, tetrahydrofuranyl, oxiranyl, aziridinyl, morpholinyl, pyrrolidinyl, piperidinyl, thiazolidinyl, and others. The terms "heterocycle", "heterocyclic ring system," and "heterocyclyl" also include partially unsaturated ring structures such as dihydrofuranyl, dihydropyrrolyl, pyrazolinyl, imidazolinyl, pyrrolinyl, chromanyl, dihydrothienyl, and others. The term "heterocycle", "heterocyclic ring system," and "heterocyclyl" also include aromatic structures such as pyridyl, pyrimidinyl, pyridazinyl, pyrazinyl, thienyl, furanyl, pyrrolyl, pyrazolyl, imidazolyl, oxazolyl, isoxazolyl, thiazolyl, isothiazolyl, triazolyl, oxadiazolyl, thiadiazolyl, and tetrazolyl, optionally substituted.

The term "heteroaromatic ring" refers to an aromatic heterocyclic ring. Examples of "heteroaromatic ring" include pyridyl, pyrimidinyl, pyridazinyl, pyrazinyl, thionyl, furanyl, pyrrolyl, pyrazolyl, imidazolyl, oxazolyl, isoxazolyl, thiazolyl, isothiazolyl, triazolyl, oxadiazolyl, thiadiazolyl, and tetrazolyl, optionally substituted.

The term "ring" or "ring system" according to the present invention refers to ring systems comprising saturated, unsaturated or aromatic carbocyclic ring systems which contain optionally at least one heteroatom as ring member and which are optionally at least mono-substituted. Said ring systems may be condensed to other carbocyclic ring systems.

The term "monocyclic ring" refers to a ring system composed of a single ring.

The term "polycyclic ring" refers to a ring system composed of at least two rings.

The term "salt" must be understood as any form of an active compound used in accordance with this invention in which the said compound is in ionic form or is charged and coupled to a counter-ion (a cation or anion) or is in solution. This definition also includes quaternary ammonium salts and complexes of the active molecule with other molecules and ions, particularly complexes formed via ionic interactions. The definition particularly includes physiologically acceptable salts. This term must be understood as equivalent to "pharmaceutically acceptable salts".

The term "pharmaceutically acceptable salts" in the context of this invention means any salt that is tolerated physiologically (normally meaning that it is not toxic, particularly as a result of the counter-ion) when used in an appropriate manner for a treatment, particularly applied or used in humans and/or mammals. These pharmaceutically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are particularly preferred, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), especially including hydrates and alcoholates, for example methanolate.

The term "prodrug" is used in its broadest sense and encompasses those derivatives that are converted in vivo to the compounds of the invention. Examples of prodrugs include, but are not limited to, derivatives and metabolites of the compounds of formula (I) that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley) and "Design and Applications of Prodrugs" (H. Bundgaard ed., 1985, Harwood Academic Publishers).

The terms "prevention", "preventing", "preventive" "prevent" and "prophylaxis" refer to the capacity of a therapeutic to avoid, minimize or difficult the onset or development of a disease or condition before its onset.

The terms "treating" or "treatment" is meant at least a suppression or an amelioration of the symptoms associated with the condition afflicting the subject, where suppression and amelioration are used in a broad sense to refer to at least a reduction in the magnitude of a parameter, e.g., symptom associated with the condition being treated, such as pain. As such, the method of the present invention also includes situations where the condition is completely inhibited, terminated, such that the subject no longer experiences the condition.

A particular embodiment of the invention compounds of formula (I) are represented by general formula (Ia):

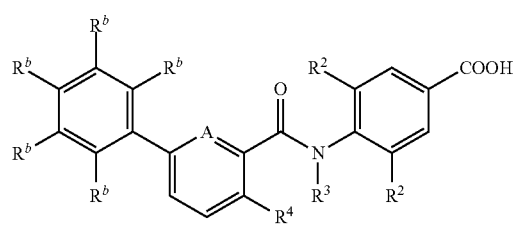

where $R^2$, $R^3$, $R^4$, $R^b$ and A have the same meanings as for general formula (I).

In another particular embodiment of the invention compounds of formula (I) are represented by general formula (Ib):

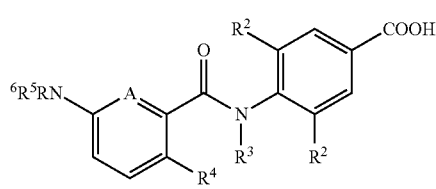

where $R^2$, $R^3$, $R^4$, $R^5$, $R^6$ and A have the same meanings as for general formula (I).

Yet another particular embodiment of the invention is that where compounds of formula (I) are represented by general formula (Ic):

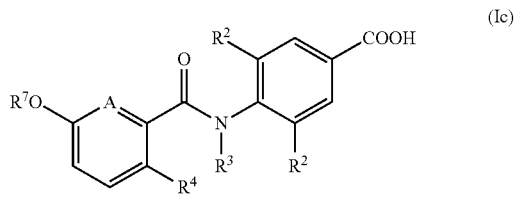

where $R^2$, $R^3$, $R^4$, $R^7$ and A have the same meanings as for general formula (I).

In a preferred embodiment of the invention one $R^1$ substituent is —COOH and the other two $R^1$ substituents are hydrogen.

In another preferred embodiment of the invention each $R^2$ is independently selected from H, methyl or Cl with the proviso that at least one $R^2$ is different from H.

In another preferred embodiment in the compounds of the invention A, B and C are such that give rise to a moiety selected from:

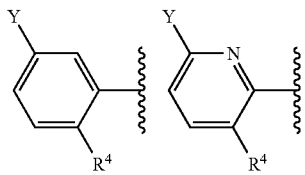

where Y has the same meanings as for general formula (I) and $R^4$ is preferably independently selected from H, methyl or Cl.

Another preferred embodiment is represented by compounds of formula (I) where Y is a —$NR^5R^6$; an —$OR^7$ or one of the following groups:

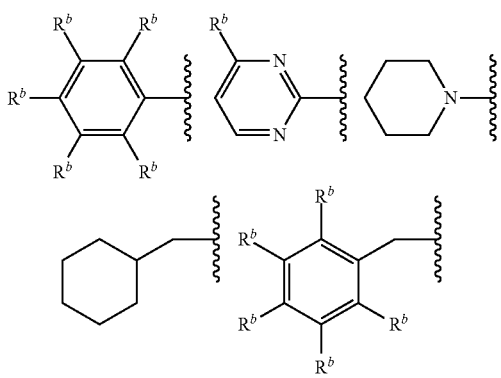

where $R^5$, $R^6$, $R^7$ and $R^b$ have the same meanings as for formula (I).

Among all the compounds encompassed by the general formula (I) the following compounds are particularly preferred:

4-(4-Chloro-3'-methoxybiphenyl-3-ylcarboxamido)-3,5-dimethylbenzoic acid;

4-(4-Chloro-3'-(hydroxymethyl)biphenyl-3-ylcarboxamido)-3,5-dimethylbenzoic acid;
4-(3'-Methoxy-4-methylbiphenyl-3-ylcarboxamido)-3,5-dimethylbenzoic acid;
4-(3'-Fluoro-4-methylbiphenyl-3-ylcarboxamido)-3,5-dimethylbenzoic acid;
4-(3'-Cyano-4-methylbiphenyl-3-ylcarboxamido)-3,5-dimethylbenzoic acid;
3,5-Dichloro-4-(3'-(hydroxymethyl)-4-methylbiphenyl-3-ylcarboxamido)benzoic acid;
3,5-Dichloro-4-(3'-cyano-4-methylbiphenyl-3-ylcarboxamido)benzoic acid;
3,5-Dichloro-4-(3'-methoxy-4-methylbiphenyl-3-ylcarboxamido)benzoic acid;
4-(3'-(Hydroxymethyl)-4-methylbiphenyl-3-ylcarboxamido)-3,5-dimethylbenzoic acid;
4-(5'-Chloro-2'-fluoro-4-methylbiphenyl-3-ylcarboxamido)-3,5-dimethylbenzoic acid;
4-(2',5'-Difluoro-4-methylbiphenyl-3-ylcarboxamido)-3,5-dimethylbenzoic acid;
4-(2',5'-Difluoro-4-methylbiphenyl-3-ylcarboxamido)-3,5-dimethylbenzoic acid;
4-(2'-fluoro-5'-methoxy-4-methylbiphenyl-3-ylcarboxamido)-3,5-dimethylbenzoic acid;
4-(3'-Carbamoyl-4-methylbiphenyl-3-ylcarboxamido)-3,5-dimethylbenzoic acid;
4-(3',4-Dichlorobiphenyl-3-ylcarboxamido)-3,5-dimethylbenzoic acid;
3,5-Dichloro-4-(3'-chloro-4-methylbiphenyl-3-ylcarboxamido)benzoic acid;
3,5-Dichloro-4-(4-chloro-3'-(hydroxymethyl)biphenyl-3-ylcarboxamido)benzoic acid;
3,5-Dichloro-4-(4-chloro-3'-methoxybiphenyl-3-ylcarboxamido)benzoic acid;
3,5-Dichloro-4-(4-chloro-3'-cyanobiphenyl-3-ylcarboxamido)benzoic acid;
3,5-Dichloro-4-(3',4-dichlorobiphenyl-3-ylcarboxamido)benzoic acid;
4-(3'-Chloro-4-methylbiphenyl-3-ylcarboxamido)-3,5-dimethylbenzoic acid;
4-(3',4-Dichlorobiphenyl-3-ylcarboxamido)-3-methylbenzoic acid;
3-Chloro-4-(3',4-dichlorobiphenyl-3-ylcarboxamido)-5-methylbenzoic acid;
4-(3-Chloro-6-(3-chlorophenyl)picolinamido)-3,5-dimethylbenzoic acid;
4-(2-Chloro-5-isobutoxybenzamido)-3,5-dimethylbenzoic acid;
3,5-Dichloro-4-(2-chloro-5-isobutoxybenzamido)benzoic acid;
3-Chloro-4-(2-chloro-5-isobutoxybenzamido)benzoic acid;
3-Chloro-4-(2-chloro-5-isobutoxybenzamido)-5-methylbenzoic acid;
4-(2-Chloro-5-isobutoxybenzamido)-3-methoxybenzoic acid;
4-(5-(Benzyloxy)-2-chlorobenzamido)-3,5-dichlorobenzoic acid;
3,5-Dichloro-4-(2-chloro-5-isopropoxybenzamido)benzoic acid;
3,5-Dichloro-4-(2-chloro-5-methoxybenzamido)benzoic acid;
3,5-Dichloro-4-(2-chloro-5-(cyclobutylmethoxy)benzamido)benzoic acid;
3,5-Dichloro-4-(2-chloro-5-ethoxybenzamido)benzoic acid;
3,5-Dichloro-4-(2-chloro-5-(neopentyloxy)benzamido)benzoic acid;
3,5-Dichloro-4-(2-chloro-5-(2,4-difluorobenzyloxyl)benzamido)benzoic acid;
3,5-Dichloro-4-(2-chloro-5-(4-chloro-2-fluorobenzyloxy)benzamido)benzoic acid;
4-(2-Chloro-5-(2,4-difluorobenzyloxyl)benzamido)-2,3,5,6-tetrafluorobenzoic acid;
3-(3'-Chloro-4-methylbiphenyl-3-ylcarboxamido)-4-methylbenzoic acid;
3-(3',4-Dichlorobiphenyl-3-ylcarboxamido)-2-methylbenzoic acid;
3-(3',4-Dichlorobiphenyl-3-ylcarboxamido)-4-methylbenzoic acid;
4-Chloro-3-(3',4-dichlorobiphenyl-3-ylcarboxamido)benzoic acid;
3-(3-Chloro-6-(3-chlorophenyl)picolinamido)-4-methylbenzoic acid;
3-(2-Chloro-5-(4-(trifluoromethyl)pyrimidin-2-yl)benzamido)-4-methylbenzoic acid;
3-(2-Chloro-5-isobutoxybenzamido)-4-methylbenzoic acid;
3-(3'-Chloro-4-methylbiphenyl-3-ylcarboxamido)-4-isopropylbenzoic acid;
3-(3',4-Dichlorobiphenyl-3-ylcarboxamido)-4-isopropylbenzoic acid;
3,5-Dichloro-4-(3-chloro-6-(3-chlorophenyl)picolinamido)benzoic acid;
3-Chloro-4-(3-chloro-6-(3-chlorophenyl)picolinamido)-5-methylbenzoic acid;
3,5-Dichloro-4-(3-chloro-6-isobutoxypicolinamido)benzoic acid;
3,5-Dichloro-4-(3-chloro-6-(cyclopropylmethylamino)picolinamido)benzoic acid;
3,5-Dichloro-4-(3-chloro-6-(cyclopentylamino)picolinamido)benzoic acid;
4-(6-(Benzylamino)-3-chloropicolinamido)-3,5-dichlorobenzoic acid;
3,5-Dichloro-4-(3-chloro-6-((2-ethoxyethyl)(methyl)amino)picolinamido)benzoic acid;
4-(6-(Butyl(methyl)amino)-3-chloropicolinamido)-3,5-dichlorobenzoic acid;
3,5-Dichloro-4-(3-chloro-6-(diethylamino)picolinamido)benzoic acid;
3,5-Dichloro-4-(3-chloro-6-(propylamino)picolinamido)benzoic acid;
3,5-Dichloro-4-(3-chloro-6-(piperidin-1-yl)picolinamido)benzoic acid;
Sodium 3,5-dimethyl-4-(4-methyl-3'-(trifluoromethyl)biphenyl-3-ylcarboxamido)benzoate;
4-(3'-Chloro-5'-methoxy-4-methylbiphenyl-3-ylcarboxamido)-3,5-dimethylbenzoic acid;
Sodium 3,5-dichloro-4-(2-chloro-5-(4-(trifluoromethyl)pyrimidin-2-yl)benzamido)benzoate;
3,5-Dichloro-4-(5-(cyclohexylmethyl)-2-methylbenzamido)benzoic acid;
4-(5-Benzyl-2-chlorobenzamido)-3,5-dichlorobenzoic acid;
3,5-Dichloro-4-(2-chloro-5-isobutylbenzamido)benzoic acid;
4-(2-Chloro-5-isobutoxy-N-methylbenzamido)-3,5-dimethylbenzoic acid;
3,5-Dichloro-4-(2-chloro-5-isobutoxy-N-methylbenzamido)benzoic acid;
3,5-Dichloro-4-(2-chloro-5-isobutoxy-N-ethylbenzamido)benzoic acid;
3,5-Dichloro-4-(2-chloro-5-isobutoxy-N-isobutylbenzamido)benzoic acid;
3,5-Dichloro-4-(2-chloro-5-isobutoxy-N-propylbenzamido)benzoic acid;

3,5-Dichloro-4-(2-chloro-5-(2,4-difluorobenzyloxy)-N-ethylbenzamido)benzoic acid;
3,5-Dichloro-4-(2-chloro-5-(4-chloro-2-fluorobenzyloxy)-N-ethylbenzamido)benzoic acid;
Sodium 3-(5-(benzyloxy)-2-chlorobenzamido)-4-methylbenzoate;
and the salts, solvates and prodrugs thereof.

In another aspect the invention refers to a process for preparing the compounds of the invention.

The compounds of the invention may be made by a variety of methods, including standard chemistry. Any previously defined variable will continue to have the previously defined meaning unless otherwise indicated. Illustrative general synthetic methods are set out below and then the preparation of specific compounds of the invention is described in more detail in the Experimental Section.

For instance, a process for preparing compounds of general formula (I) comprises the reaction between a compound of general formula (II):

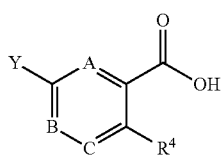

with a compound of general formula (IV), or a protected form thereof

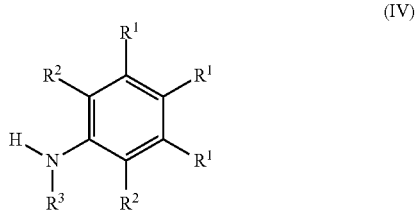

followed if necessary by the removal of any protecting group that may be present.

In general, a compound of formula IV is preferably used in protected form, i.e. if $R^1$ is —$CO_2H$, compound IV is used in protected form as an ester, and therefore the acid must be deprotected after the reaction of II with IV under standard conditions; a suitable set of conditions comprises the treatment of the corresponding ester with NaOH (10%), in tetrahydrofuran or methanol at about 50° C.

A compound of formula I thus obtained can be converted into a salt using standard procedures. For example, when $R^1$ in a compound of formula I is —$CO_2H$, the sodium salt can be obtained for example by treatment of the corresponding carboxylic acid with sodium tert-butoxide in methanol at room temperature.

The process for the synthesis of compound of general formula I can be summarised as follows:

SCHEME A

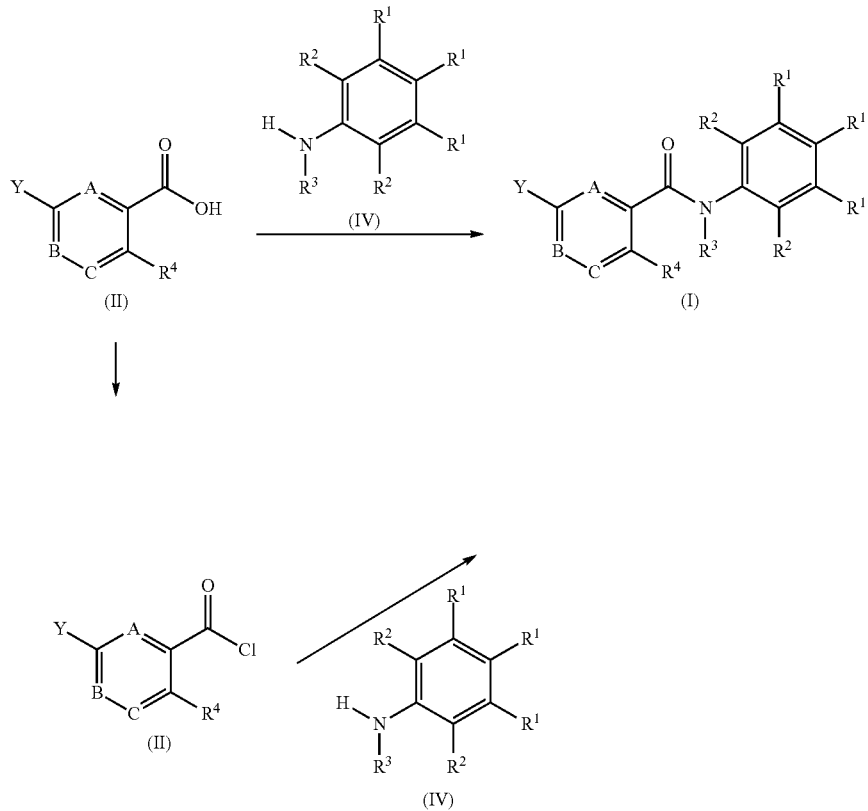

In the above scheme, A, B, C, $R^1$, $R^2$, $R^3$, and $R^4$ have the meaning previously defined.

Referring to Scheme A, compounds of formula I are prepared by amide coupling procedures. For example, acid (II) are coupled with amine (IV) directly, in the presence of an activating agent such us 1,1'-carbonyl-didimidazole (CDI), (Benzotriazol-1-yloxy)tripyrrolidinophosphonium hexafluorophosphate (PyBOP), (Dimethylamino)-N,N-dimethyl(3H-[1,2,3]triazolo[4,5-b]pyridin-3-yloxy)methaniminium hexafluorophosphate (HATU), 3-(ethyliminomethyleneamino)-N,N-dimethylpropan-1-amine/1-hydroxybenzotriazole (EDC/HOBt) or the like. Alternatively, acids (II) are activated as mixed anhydrides or acid chlorides (III), and then coupled with amides (IV) in the presence of a suitable base such as sodium hydride, triethylamine, diisopropylethylamine, pyridine or the like.

The starting compounds of general formula (II) can be prepared in several ways. The process for the synthesis of compound of general formula (IIa), where Y is a phenyl group, can be summarised as follows:

SCHEME B

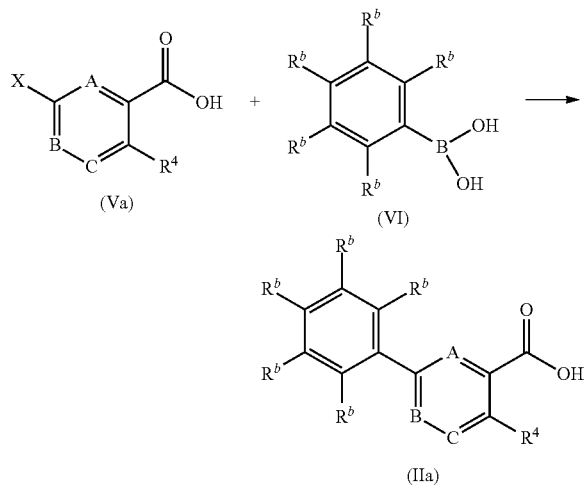

In the above scheme, X represents chloro or bromo and all remaining substituents have the same meanings as previously defined in relation to a compound of formula (I).

Suitable reaction conditions for the preparation a compound of formula (IIa) include conventional methods for Suzuki coupling between halo derivatives (Va) and boronic acids (VI) in the presence of a Pd source and a ligand. For example (Va) and (VI) are coupled by treatment with tetrakis(triphenylphosphine)palladium(0) (Pd(PPh$_3$)$_4$) in the presence of a base such a as sodium carbonate in a solvent, e.g. acetonitrile at a temperature, e.g. 80° C. Examples of other combination of Pd sources and ligands are palladium (II) acetate and triphenylphospine, dichlorobis(tripneylphosphine)palladium (II), tris(dibenylideneacetone)dipalladium (0). Other suitable bases are potassium carbonate, cesium carbonate, potassium phosphate or the like. Other preferred solvents include dioxane, tetrahydorfurane and pyridine. Temperature can be varied from room temperature to 130° C.

The process for the synthesis of compound of general formula (IIb), where Y is a $R^6R^5N$ group, can be summarised as follows:

SCHEME C

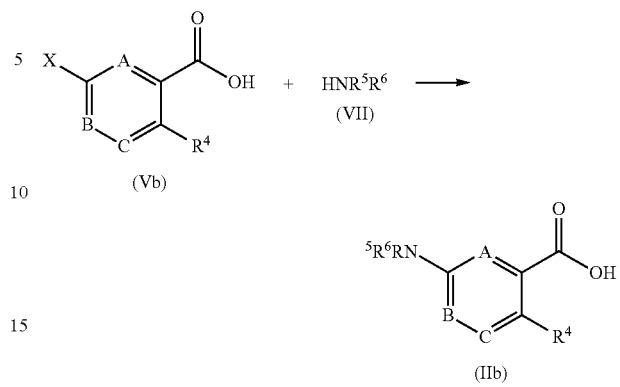

In the above scheme, X represents chloro or bromo and all remaining substituents have the same meanings as previously defined in relation to a compound of formula (I).

Suitable reaction conditions for the preparation a compound of formula (IIb) include conventional methods for halogen displacement from halo derivatives (Vb) with amines (VII). The displacement reaction can be carried out, for example, by heating in an excess of amine (VII) in the presence or without solvent with the aid of microwaves or without at a temperature between room temperature and 170° C. Both reagents can be also coupled under known conditions of Buchwald-Hartwing reaction.

The process for the synthesis of compound of general formula (IIc), where Y is a $OR^7$ group, can be summarised as follows:

SCHEME D

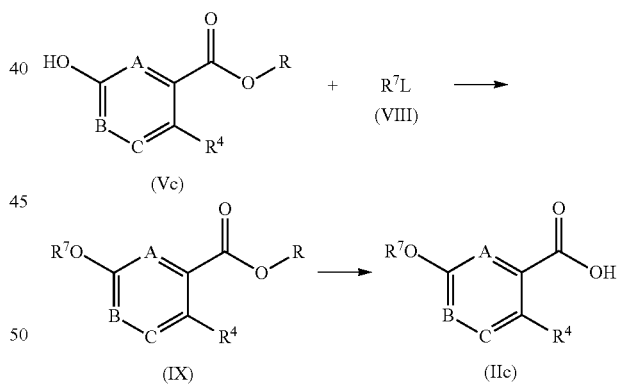

In the above scheme, L represents a good leaving group, e.g. Cl, Br, I, tosylate, mesylate, triflate, or fluorosulphonate, R is alkyl group and all remaining substituents have the same meanings as previously defined in relation to a compound of formula (I).

Suitable reaction conditions for the preparation a compound of formula (IIc) include conventional methods for the alkylation of the compounds of formula (Vc) with alkylating agents (VIII) to form an ether (IX) followed by ester hydrolysis. The alkylation reaction of the compounds of formula (Vc) and (VIII) may be carried out in an organic solvent such as acetonitrile, tetrahydrofuran or dimethylformamide at ambient or elevated temperature, optionally in the presence of a suitable base such as potassium or cesium carbonate. Finally ester (IX) is hydrolysed under standard conditions to give (IIc); a suitable set of conditions comprises the treatment of the corresponding ester with NaOH (10%), in tetrahydrofuran or methanol at about 50° C.

The process for the synthesis of compound of general formula (IId), where Y is a benzyl, $C_{1-6}$-alkyl or $C_{1-4}$alkylene-$C_{3-6}$-cycloalkyl group, can be summarised as follows:

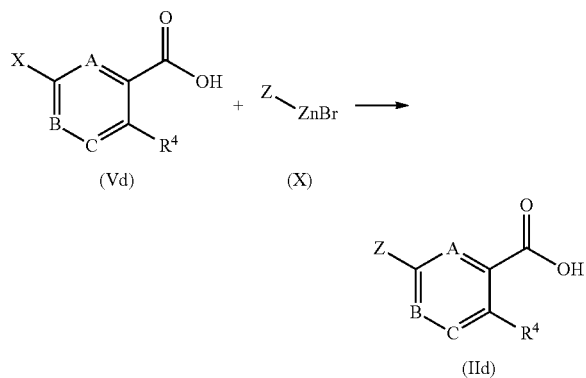

In the above scheme X, represents chloro or bromo, Z represents benzyl, $C_{1-6}$-alkyl or $C_{1-4}$alkylene-$C_{3-6}$-cycloalkyl group and all remaining substituents have the same meanings as previously defined in relation to a compound of formula (I).

Suitable reaction conditions for the preparation a compound of formula (IId) include conventional methods for Negishi coupling of an organozinc reagent (X) and an aryl or heteroaryl halide (Vd) in the presence of a Pd source and a ligand. For example (X) and (Vd) are coupled by treatment with palladium(II) acetate and tri-tert-butylphosphine in a solvent, e.g. N-metilpirrolidine at a temperature, e. g. of 100° C. Other metal complexes with, for example, Mg, Sn or Si can be also used for this coupling.

Compounds of formula (Va), (Vb), (Vc), (Vd), (VI), (VII), (VIII) and (X), are either commercially available or can be obtained by conventional methods.

Certain substituents in any of the reaction intermediates described above and in the compounds of formula (I) may be converted to other substituents by conventional methods known to those skilled in the art, Richard Larock, *Comprehensive Organic Transformations,* 2nd edition, Wiley-VCH, ISBN 0-471-19031-4.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly. In some instances it may be appropriate to use protecting groups to prevent reactions between one or more groups or moieties. Such procedures are familiar to those skilled in the art (see, for example, "Protective groups in organic synthesis" by T. W. Greene and P. G. M. Wuts (John Wiley & sons 10 1999) or "Protecting Groups" by P. J. Kocienski (Georg Thieme Verlag 1994).

An additional aspect of the invention relates to the therapeutic use of the compounds of general formula (I). As mentioned above, compounds of general formula (I) show a strong affinity to EP4 receptors. For this reason, they are suitable for the treatment and/or the prophylaxis of disorders and diseases mediated by EP4 receptors.

Compounds of the invention are particularly useful for modulating pain. The compounds of the present invention can treat or prevent the pain associated with several pathological conditions comprising, among others, inflammatory related pain (Oka et al. 1997; Lin et al. 2006 and Jones et al. 2009) including low back and neck pain, skeletal pain, post-partum pain, toothache, sprains and straits, myositis, neuralgia, synovitis, arthritis, including rheumatoid arthritis, degenerative joint diseases (osteoarthritis), gout and ankylosing spondylitis, bursitis, burns including radiation and corrosive chemical injuries and sunburns; postoperative pain including dental procedures; neuropathic pain; visceral pain; tension headache; cluster headaches; migraine and the like.

Moreover, by inhibition of prostanoid-induced smooth muscle contraction by antagonizing contractile prostanoids or mimicking relaxing prostanoids, EP4 modulators may be used in the treatment of motility-related disorders (with or without pain) such as gastroinstestinal disorders and urinary incontinence and other urinary tract diseases (Chuang et al. 2012), dysmenorrhea and preterm labour.

The compounds of the invention can also be useful in prostaglandin-mediated proliferation disorders such as in diabetic retinopathy and tumour angiogenesis, cancer (Cherukuri et al. 2007), the inhibition of cellular neoplasic transformations and metastatic tumour growth.

They can further be used in the treatment of neurodegenerative diseases (including senile dementia, Alzheimer's disease, Pick's disease, Huntingdon's chorea, Parkinson's disease, Creutzfeldt-Jakob disease, or Amyotrophic Lateral Sclerosis) (Wei et al. 2010), neuroprotection/stroke, glaucoma, bone loss (osteoporosis) and the proportion of bone formation (treatment of fractures) and other bone diseases such as Paget's disease.

Compounds of the invention are also particularly useful for modulating immune response and inflammation (Zimecki et al., 2012; Takayama et al., 2006; McCoy et al., 2002; Jones et al., 2009; Yao C. et al., 2009). Compounds of the present invention can be useful for modulating inflammatory diseases including the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome pigeon fanciers disease, farmer's lung, CORD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ tnasplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome; bone diseases characterized by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis; immune diseases such as multiple sclerosis, rheumatoid arthritis, inflammatory bowel diseases and allergic skin disorders; contact hypersensitivity, cough and endometriosis.

Compounds of the present invention may have therapeutic utility in the treatment of migraine since it has been observed that EP4 antagonists block $PGE_2$-induced relaxation of human-isolated middle cerebral artery (Davis et al., 2004; Maubach et al., 2009) and the picture has been enlarged to include the interaction of endogenous $PGE_2$ with calcitonin gene-related peptide release from trigeminal nerves (Maubach et al., 2009).

The compounds of the present invention can also have effect on modulation of the cough reflex (Maher et al 2010) and treatment for endometriosis in women (Lee et al 2010).

In this sense, compound of general formula (I) for use in the treatment and/or prophylaxis of diseases or disorders mediated by the EP4 receptor. This includes but is not limited to diseases such as inflammatory related pain including low back and neck pain, skeletal pain, post-partum pain, toothache, sprains and straits, myositis, neuralgia, synovitis, arthritis, including rheumatoid arthritis, degenerative joint diseases, gout and ankylosing spondylitis, bursitis, burns including radiation and corrosive chemical injuries and sunburns; postoperative pain; neuropathic pain; visceral pain; tension headache; cluster headaches; migraine; motility-related disorders including gastrointestinal disorders, urinary incontinence and other urinary tract diseases; dysmenorrhea; preterm labour; diabetic retinopathy; tumour angiogenesis; cancer; metastatic tumour growth; neurodegenerative diseases including senile dementia, Alzheimer's disease, Pick's disease, Huntington's chorea, Parkinson's disease, Creutzfeldt-Jakob disease, or amyotrophic lateral sclerosis; neuroprotection/stroke; glaucoma; osteoporosis; bone fractures; Paget's disease; hyperthermia including different types of fever as rheumatic fever; symptoms associated with influenza or other viral infections; gastrointestinal disorders related with chemotherapy or irritable bowel syndrome; gastrointestinal bleeding; coagulation disorders including anaemia, hypoprothrombinemia, haemophilia or other bleeding problems; kidney diseases including nephritis, particularly mesangial proliferative glomerulonephritis and nephritic syndrome; thrombosis and occlusive vascular diseases; inflammatory diseases including the treatment of skin conditions such as, bums, eczema, dermatitis, psoriasis; ophthalmic diseases including glaucoma, retinitis, retinopathies, uveitis and of acute injury to the eye tissue such as conjunctivitis; lung disorders including asthma, bronchitis, emphysema, allergic rhinitis, respiratory distress syndrome pigeon fancier's disease, farmers lung, CORD; gastrointestinal tract disorders including aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease; organ tnasplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome; bone diseases characterized by abnormal bone metabolism or resorption such as osteoporosis, especially postmenopausal osteoporosis, hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis, especially urolithiasis, solid carcinoma, gout and ankylosing spondylitis, tendinitis and bursitis; immune diseases such as multiple sclerosis, rheumatoid arthritis, inflammatory bowel diseases and allergic skin disorders; contact hypersensitivity, cough and endometriosis.

A related aspect refers to the use of at least one compound of general formula (I) for the manufacture of a medicament for the treatment and/or prophylaxis diseases or disorders mediated by EP4 receptors or in which EP4 receptors are involved.

In one embodiment, the EP4-mediated disease or disorder is selected from the group consisting of inflammatory related pain including low back and neck pain, skeletal pain, post-partum pain, toothache, sprains and straits, myositis, neuralgia, synovitis, arthritis, including rheumatoid arthritis, degenerative joint diseases, gout and ankylosing spondylitis, bursitis, burns including radiation and corrosive chemical injuries and sunburns; postoperative pain; neuropathic pain; visceral pain; tension headache; cluster headaches; migraine; motility-related disorders including gastrointestinal disorders, urinary incontinence and other urinary tract diseases; dysmenorrhea; preterm labour; diabetic retinopathy; tumour angiogenesis; cancer; metastatic tumour growth; neurodegenerative diseases including senile dementia, Alzheimer's disease, Pick's disease, Huntington's chorea, Parkinson's disease, Creutzfeldt-Jakob disease, or amyotrophic lateral sclerosis; neuroprotection/stroke; glaucoma; osteoporosis; bone fractures; Paget's disease; hyperthermia including different types of fever as rheumatic fever; symptoms associated with influenza or other viral infections; gastrointestinal disorders related with chemotherapy or irritable bowel syndrome; gastrointestinal bleeding; coagulation disorders including anaemia, hypoprothrombinemia, haemophilia or other bleeding problems; kidney diseases including nephritis, particularly mesangial proliferative glomerulonephritis and nephritic syndrome; thrombosis and occlusive vascular diseases; inflammatory diseases including the treatment of skin conditions such as sunburn, bums, eczema, dermatitis, psoriasis; ophthalmic diseases such as glaucoma, retinitis, retinopathies, uveitis and of acute injury to the eye tissue including conjunctivitis; lung disorders including asthma, bronchitis, emphysema, allergic rhinitis, respiratory distress syndrome pigeon fancier's disease, farmer's lung, CORD; gastrointestinal tract disorders including aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease; organ tnasplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome; bone diseases characterized by abnormal bone metabolism or resorption such as osteoporosis especially postmenopausal osteoporosis, hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis especially urolithiasis, solid carcinoma, gout and ankylosing spondylitis, tendinitis and bursitis; immune diseases such as multiple sclerosis, rheumatoid arthritis, inflammatory bowel diseases and allergic skin disorders; contact hypersensitivity, cough and endometriosis.

An aspect of the invention related to the therapeutic use of the compounds of general formula (I) is a method of treatment and/or prophylaxis of disorders and diseases mediated by EP4 receptors which comprises administering to a patient in need thereof a therapeutically effective amount of at least one compound of general formula (I). In one embodiment, the EP4-mediated disease or disorder is selected from the group consisting of inflammatory related pain including low back and neck pain, skeletal pain, post-partum pain, toothache, sprains and straits, myositis, neuralgia, synovitis, arthritis, including rheumatoid arthritis, degenerative joint diseases, gout and ankylosing spondylitis, bursitis, burns including radiation and corrosive chemical injuries and sunburns; postoperative pain; neuropathic pain; visceral pain; tension headache; cluster headaches; migraine; motility-related disorders including gastrointestinal disorders, urinary incontinence and other urinary tract diseases; dysmenorrhea; preterm labour; diabetic retinopathy; tumour angiogenesis; cancer; metastatic tumour growth; neurodegenerative diseases including senile dementia, Alzheimer's disease, Pick's disease, Huntington's chorea, Parkinson's disease, Creutzfeldt-Jakob disease, or amyotrophic lateral sclerosis; neuroprotection/stroke; glaucoma; osteoporosis; bone fractures; Paget's disease; hyperthermia including different types of fever as rheumatic fever; symptoms associated with influenza or other viral infections; gastrointestinal disorders related with chemotherapy or irritable bowel syndrome; gastrointestinal bleeding; coagulation disorders including anaemia, hypoprothrombinemia, haemophilia or other bleeding problems; kidney diseases including nephritis, particularly mesangial proliferative glomerulonephritis and nephritic syndrome; thrombosis and occlusive vascular diseases; inflammatory diseases including the treatment of skin conditions such as, bums, eczema, dermatitis, psoriasis; ophthalmic diseases including glaucoma, retinitis, retinopathies, uveitis and of acute injury to the eye tissue such as conjunctivitis; lung disorders including asthma, bronchitis, emphysema, allergic rhinitis, respiratory distress syndrome pigeon fancier's disease, farmers lung, CORD; gastrointestinal tract disorders including aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease; organ trasplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome; bone diseases characterized by abnormal bone metabolism or resorption such as osteoporosis, especially postmenopausal osteoporosis, hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis, especially urolithiasis, solid carcinoma, gout and ankylosing spondylitis, tendinitis and bursitis; immune diseases such as multiple sclerosis, rheumatoid arthritis, inflammatory bowel diseases and allergic skin disorders; contact hypersensitivity, cough and endometriosis.

The amount of active ingredient that must be administered to the patient depends on the patient's weight, the type of application, the condition and severity of the disease. Normally, in human beings 1 to 1500 mg of the active compound is administered daily in one or several doses.

A further aspect of the invention regards a pharmaceutical composition which comprises a compound of general formula (I), and at least a pharmaceutically acceptable carrier, additive, adjuvant or vehicle.

The auxiliary materials or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

Suitable preparations for oral applications are tablets, pills, chewing gums, capsules, granules, drops or syrups. Suitable preparations for parenteral applications are solutions, suspensions, reconstitutable dry preparations or sprays.

The compounds of the invention are formulated as deposits in dissolved form or in patches, for percutaneous application.

Skin applications include ointments, gels, creams, lotions, suspensions or emulsions.

The preferred form of rectal application is by means of suppositories.

EXPERIMENTAL SECTION

The following abbreviations have been used in the examples:
AcN: acetonitrile
DCM: dichloromethane
DIPEA: N,N-diisopropylethylamine
DMF: N,N-dimethylformamide
Et$_2$O: diethyl ether
EtOAc: ethyl acetate
EtOH: ethanol
LC-MS: liquid chromatography-mass spectroscopy
MeI: iodomethane
MeOH: methanol
NMP: N-methylpyrrolidone
Pd(AcO)$_2$: palladium acetate
Pd(PPh$_3$)$_4$: tetrakis(triphenylphosphine)palladium(0)
PtBu$_3$: tri tert-butyl phosphine
THF: tetrahydrofurane
TLC: thin layer chromatography
t$_R$: retention time
UPLC: Ultra performance liquid chromatograph The following method was used to determine the LC-MS spectrums:
Method 1:
Column Waters Acquity UPLC BEH C18 (1.7 µm, 2.1 mm×50 mm), temperature: 40° C., flow: 0.5 mL/min, eluent:

ACN (A)/ammonium bicarbonate 10 mM (B), gradient: 0 min 10% A—3.75 min 90% A

Intermediate compound 1: Ethyl 4-amino-3,5-dichlorobenzoate

To a suspension of 4-amino-3,5-dichlorobenzoic acid (5 g, 24.27 mmol) in EtOH (40 mL), thionyl chloride (3.17 mL, 43.7 mmol) was added. The reaction mixture was stirred at 60° C. for 18 h. Organic solvents were evaporated under reduced pressure. The residue was diluted with water and extracted twice with EtOAc. The combined organic phases were dried over $Na_2SO_4$ and concentrated to dryness, providing the title compound with quantitative yield.

LC-MS (method 1): $t_R$=2.38 min; m/z=232(MH$^+$).

Following a similar procedure to that described for intermediate compound 1, but using in each case the corresponding starting materials, the following compounds were obtained:

| Intermediate compound | Name | Starting Materials | UPLC method | $t_R$ (min) | m/z |
|---|---|---|---|---|---|
| 1a | Ethyl 4-amino-3-chloro-5-methylbenzoate | 4-amino-3-chloro-5-methylbenzoic acid | 1 | 2.21 | 214 |
| 1b | Ethyl 4-amino-3-methoxybenzoate | 4-amino-3-methoxybenzoic acid | 1 | 1.78 | 196 |

Intermediate compound 2: Ethyl 4-amino-3,5-dimethylbenzoate a) Ethyl 3,5-dimethyl-4-nitrobenzoate

To a solution of 3,5-dimethyl-4-nitrobenzoic acid (5 g, 25.6 mol) in EtOH (50 mL), thionyl chloride (3.35 mL, 46.1 mmol) was added. The reaction mixture was stirred at 60° C. for 18 h. The solvent was evaporated to dryness and the reaction crude was used in next step without further purification b) Title Compound

To a solution of the compound obtained in the previous section (5.7 g, 25.6 mmol) in EtOAC/EtOH 1:1 (50 mL), Pd/C 10% (1.0 g) was added. The reaction mixture was purged, filled with hydrogen and stirred at room temperature overnight. The reaction mixture was filtered through a plug of Celite® and evaporated to dryness to afford 3.0 g of the desired product (60.8% yield)

LC-MS (method 1): $t_R$=1.99 min; m/z=194 (MH$^+$).

Intermediate compound 3: Ethyl 4-(5-bromo-2-chlorobenzamido)-3,5-dimethylbenzoate a) 5-Bromo-2-chlorobenzoyl chloride

To a solution of 5-bromo-2-chlorobenzoic acid (2 g, 8.49 mmol) in dichloromethane (25 mL), oxallyl chloride (1.26 mL, 14.44 mmol) and a catalytic amount (two drops) of DMF were added. The reaction mixture was stirred at room temperature overnight. The solvent was evaporated to dryness and the reaction crude was used in next step without further purification.

b) Title Compound

To a solution of the compound obtained in the previous section (1.5 g, 5.95 mmol) in DMF (30 mL) at 0° C., reference example 2 (1.38 g, 7.14 mmol) and DIPEA (1.55 mL, 8.93 mmol) were added. The reaction mixture was then stirred at room temperature overnight. The solvent was concentrated off. The crude residue was dissolved in EtOAc and washed with 1N NaOH aqueous solution (3×20 mL) and 3N HCl aqueous solution (3×20 mL). The combined organic phases were dried over $Na_2SO_4$ and concentrated to dryness. The resulting solid was suspended in $Et_2O$ (10 mL) for 10 minutes and filtered to afford 1.32 g (54.2% yield) of the desired compound.

LC-MS (method 1): $t_R$=2.52 min; m/z=412 (MH$^+$).

Following a similar procedure to that described for intermediate compound 3, but using the corresponding starting materials, the following compound was obtained:

| Intermediate compound | Name | Starting Materials | UPLC method | $t_R$ (min) | m/z |
|---|---|---|---|---|---|
| 3a | Ethyl 4-(5-bromo-2-methylbenzamido)-3,5-dimethylbenzoate | 5-bromo-2-methylbenzoic acid and intermediate compound 2 | 1 | 2.56 | 390 |

Intermediate compound 4: 4-(5-Bromo-2-chlorobenzamido)-3,5-dichlorobenzoic acid To a solution of intermediate compound 1 (230 mg, 0.98 mmol) in DMF (6 mL) at −10° C., 55% NaH dispersion in mineral oil (70 mg, 2.96 mmol) was added and the resulting suspension was stirred at room temperature for 10 min. Then a solution of the intermediate compound 3 section a (250 mg, 0.98 mmol) in DMF was added. The resulting mixture was stirred at room temperature overnight. The reaction mixture was quenched by adding 1N HCl aqueous solution (5 mL) and extracted twice with EtOAc. The combined organic phases were dried over $Na_2SO_4$ and concentrated to dryness. The resulting solid was suspended in MeOH/DCM 1:1 (10 mL) for 10 minutes and filtered to afford 200 mg (48.0% yield) of the desired compound.

LC-MS (method 1): $t_R$=4.25 min; m/z=425 (MH$^+$).

Following a similar procedure to that described for intermediate compound 4, but using the corresponding starting materials, the following compound was obtained:

| Intermediate compound | Name | Starting Materials | UPLC method | $t_R$ (min) | m/z$^-$ |
|---|---|---|---|---|---|
| 4a | 3,5-Dichloro-4-(3,6-dichloropicolinamido)-benzoic acid | 3,6-dichloropicolinic acid and reference example 1 | 1 | 1.36 | 379 |

Intermediate compound 5: Ethyl 4-(5-bromo-2-methyl benzamido)-3,5-dichlorobenzoate To a solution of intermediate compound 1 (1.71 g, 7.31 mmol) in DMF (30 mL) at −10° C., 55% NaH dispersion in mineral oil (0.95 g, 21.9 mmol) was added and the resulting suspension was stirred at room temperature for 30 min. Then a solution of 5-bromo-2-methylbenzoyl chloride (1.71 g, 7.338 mmol) in THF (10 mL) was added. The resulting mixture was stirred at room temperature overnight. The reaction mixture was quenched by adding 2N NaOH aqueous solution (15 mL) and extracted twice with EtOAc. The combined organic phases were dried over $Na_2SO_4$ and concentrated to dryness. The resulting solid was suspended in $Et_2O$ (40 mL) for 10 minutes and filtered to afford 1.49 g (47.3% yield) of the desired compound.

LC-MS (method 1): $t_R$=2.73 min; m/z=432 (MH$^+$).

Intermediate compound 6:
3'-Chloro-4-methylbiphenyl-3-carboxylic acid

To a suspension of 5-bromo-2-methylbenzoic acid (4000 mg, 18.6 mmol) in AcN (40 mL) under Ar atmosphere, 3-chlorophenylboronic acid (4360 mg, 27.9 mmol), Pd(PPh$_3$)$_4$ (1075 mg, 0.93 mmol), and 2M $Na_2CO_3$ aqueous solution (28 mL, 55.8 mmol) were added. The reaction mixture was stirred at 80° C. for 18 h. Organic solvents were evaporated under reduced pressure. The aqueous layer was washed twice with EtOAc and the pH of the solution was adjusted to 2 by adding 10% HCl aqueous solution. The resulting mixture was filtered and the collected solids were washed with water and dried overnight in the oven to afford 3360 mg of the desired product (73.2% yield).

LC-MS (method 1): $t_R$=1.46 min; m/z=245 (MH$^-$).

Following a similar procedure to that described for intermediate compound 6, but using in each case the corresponding starting materials, the following compounds were obtained:

| Intermediate compound | Name | Starting Materials | UPLC method | $t_R$ (min) | m/z$^-$ |
|---|---|---|---|---|---|
| 6a | 3',4-Dichloro-biphenyl-3-carboxylic acid | 5-bromo-2-chlorobenzoic acid and 3-chloro-phenylboronic acid | 1 | 1.41 | 265 |
| 6b | 3-Chloro-6-(3-chloro-phenyl)picolinic acid | 3,6-dichloropicolinic acid and 3-chlorophenyl-boronic acid | 1 | 1.25 | 266 |
| 6c | 2-Chloro-5-(4-(trifluoro-methyl)pyrimidin-2-yl)benzoic acid | 2-chloro-4-(trifluoro-methyl)pyrimidine and 5-borono-2-chlorobenzoic acid | 1 | 1.27 | 301 |

Intermediate compound 7: Ethyl 3,5-dichloro-4-(3,6-dichloropicolinamido)benzoate Following a similar procedure to that described for intermediate compound 1, but using intermediate compound 4a as starting material, the desired compound was obtained.

LC-MS (method 1): $t_R$=2.63 min; m/z=409 (MH$^+$).

Intermediate compound 8:
2-Chloro-5-isobutoxybenzoic acid a) Ethyl 2-chloro-5-hydroxybenzoate Following a similar procedure to that described for intermediate compound 1, but using 2-chloro-5-hydroxybenzoic acid instead of 4-amino-3,5-dichlorobenzoic acid, the desired compound was obtained.

b) Ethyl 2-chloro-5-isobutoxybenzoate

To a solution of the compound obtained in the previous section (2 g, 9.97 mmol) and $Cs_2CO_3$ (9.74 g, 29.9 mmol) in AcN (100 mL), 1-bromo-2-methylpropane (1.62 mL, 14.95 mmol) was added at room temperature. The mixture was refluxed overnight. The solvent was concentrated off. It was diluted with water and extracted with EtOAc (3×50 mL). The combined organic phases were dried over $Na_2SO_4$ and concentrated to dryness to give 2.31 g of the desired product (90% yield).

c) Title Compound

To a solution of the compound obtained in the previous section (3.28 g, 12.4 mmol) in MeOH (150 mL) a solution of 20% NaOH aqueous solution (20 mL, 124 mmol) was added at room temperature. The mixture was refluxed for 4 h. The solvent was concentrated off. It was diluted with water and 1N HCl aqueous solution was added until acid pH was reached and extracted with EtOAc (3×50 mL). The combined organic phases were dried over $Na_2SO_4$ and concentrated to dryness to give 2.85 g of the desired product (100% yield).

LC-MS (method 1): $t_R$=1.30 min; m/z=227 (MH$^-$).

Following a similar procedure to that described intermediate compound 8, but using the corresponding starting materials, the following compound was obtained:

| Intermediate compound | Name | Starting Materials | UPLC method | $t_R$ (min) | m/z$^-$ |
|---|---|---|---|---|---|
| 8a | 5-(Benzyloxy)-2-chlorobenzoic acid | benzyl bromide | 1 | 1.37 | 261 |

Intermediate compound 9:
5-(Cyclohexylmethyl)-2-methylbenzoic acid

To a solution of 5-bromo-2-methylbenzoic acid (600 mg, 2.79 mmol) in NMP (6 mL) under Ar atmosphere, 0.5 M (cyclohexylmethyl)zinc(II) chloride solution in THF (16.7 mL, 8.37 mmol), Pd(AcO)$_2$ (31 mg, 0.14 mmol), and 1M PtBu$_3$ solution in toluene (0.28 mL, 0.28 mmol) were added. The reaction mixture was stirred at 100° C. for 18 h. Organic solvents were evaporated under reduced pressure. The aqueous layer was washed twice with EtOAc and water. The combined organic phases were dried over $Na_2SO_4$ and concentrated to dryness. The crude residue was cromatographed on a silica gel flash system (Biotage SP1) using hexane/EtOAC mixtures of increasing polarity as eluent to afford 468 mg of the desired product (72.2% yield).

LC-MS (method 1): $t_R$=1.71 min; m/z=231 (MH$^-$).

Following a similar procedure to that described for intermediate compound 9, but using in each case the corresponding starting materials, the following compounds were obtained:

| Intermediate compound | Name | Starting Materials | UPLC method | $t_R$ (min) | m/z⁻ |
|---|---|---|---|---|---|
| 9a | 5-Benzyl-2-chlorobenzoic acid | 5-bromo-2-chlorobenzoic acid and benzylzinc(II) bromide | 1 | 1.37 | 245 |
| 9b | 2-Chloro-5-isobutylbenzoic acid | 5-bromo-2-chlorobenzoic acid and isobutylzinc(II) bromide | 1 | 1.36 | 211 |

Intermediate compound 10: Ethyl 3-amino-4-isopropyl benzoate a) 4-Isopropyl-3-nitrobenzoic acid To a solution of 4-isopropylbenzoic acid (0.5 g, 3.05 mmol) in $H_2SO_4$ at −10° C., a mixture of $H_2SO_4/HNO_3$ 1:1 (2 ml) was added slowly. The reaction mixture was stirred at −10° C. for 1 h. The slurry was poured into ice water and the solid was filtered off, washed with cold water and dried to give 580 mg of the desired product (91% yield).

b) Ethyl 4-isopropyl-3-nitrobenzoate

Following a similar procedure to that described for intermediate compound 1, but using the compound obtained in the previous section, instead of 4-amino-3,5-dichlorobenzoic, the desired compound was obtained. The reaction crude was used in next step without further purification.

c) Title Compound

A solution of the compound obtained in the previous section (340 mg, 1.43 mmol) in EtOAc (28 mL) was hydrogenated with the H-cube apparatus (Pd/C, 1 mL/min, 40° C.). The resulting solution was concentrated to dryness to give 300 mg of the title compound (100% yield) which can be used in the next step without further purification.

LC-MS (method 1): $t_R$=2.24 min; m/z=208 (MH⁺).

Example 1: 4-(4-Chloro-3'-methoxybiphenyl-3-ylcarboxamido)-3,5-dimethylbenzoic acid a) Ethyl 4-(4-chloro-3'-methoxybiphenyl-3-ylcarboxamido)-3,5-dimethylbenzoate To a solution of intermediate compound 3 (150 mg, 0.365 mmol) in MeOH (3 mL) under Ar atmosphere, 3-methoxyphenylboronic acid (56 mg, 0.365 mmol), Pd(AcO)$_2$ (1.02 mg, 4.57 mol), and 2M $Na_2CO_3$ aqueous solution (0.36 mL, 0.73 mmol) were added. The reaction mixture was heated in a Biotage microwave oven at 140° C. for 30 minutes. The reaction mixture was filtered through a plug of Celite® and the solvents were evaporated under reduced pressure. The crude residue was cromatographed on a silica gel flash system (Biotage SP1) using hexane/EtOAC mixtures of increasing polarity as eluent to afford 64 mg of the desired product (40 yield).

LC-MS (method 1): $t_R$=2.71 min; m/z=438 (MH⁺).

b) Title Compound

To a solution of the compound obtained in the previous section (64 mg, 0.146 mmol) in THF (2 mL) a solution of 2N NaOH aqueous solution (0.73 mL, 0.146 mmol) was added at room temperature. The mixture was stirred at 80° C. overnight. The solvent was concentrated off. It was diluted with water and 1N HCl aqueous solution was added until acid pH was reached. The suspension was cooled down to 0° C. and the solid was filtered off, washed with cold water and dried to give 25 mg of the desired product (42% yield).

LC-MS (method 1): $t_R$=1.68 min; m/z=410 (MH⁺).

Following a similar procedure to that described in example 1, but using in each case the corresponding starting materials, the following compounds were obtained:

| Example | Name | Starting Materials | UPLC method | $t_R$ (min) | m/z |
|---|---|---|---|---|---|
| 2 | 4-(4-Chloro-3'-(hydroxymethyl)biphenyl-3-ylcarboxamido)-3,5-dimethylbenzoic acid | intermediate compound 3 and 3-(hydroxymethyl)phenylboronic acid | 1 | 1.38 | 410 |
| 3 | 4-(3'-Methoxy-4-methylbiphenyl-3-ylcarboxamido)-3,5-dimethylbenzoic acid | intermediate compound 3a and 3-methoxyphenylboronic acid | 1 | 1.69 | 390 |
| 4 | 4-(3'-Fluoro-4-methylbiphenyl-3-ylcarboxamido)-3,5-dimethylbenzoic acid | intermediate compound 3a and 3-fluorophenylboronic acid | 1 | 1.72 | 378 |
| 5 | 4-(3'-Cyano-4-methylbiphenyl-3-ylcarboxamido)-3,5-dimethylbenzoic acid | intermediate compound 3a and 3-cyanophenylboronic acid | 1 | 1.58 | 385 |
| 6 | 3,5-Dichloro-4-(3'-(hydroxymethyl)-4-methylbiphenyl-3-ylcarboxamido)benzoic acid | intermediate compound 5 and 3-(hydroxymethyl)phenylboronic acid | 1 | 1.47 | 430 |
| 7 | 3,5-Dichloro-4-(3'-cyano-4-methylbiphenyl-3-ylcarboxamido)benzoic acid | intermediate compound 5 and 3-cyanophenylboronic acid | 1 | 1.68 | 425 |
| 8 | 3,5-Dichloro-4-(3'-methoxy-4-methylbiphenyl-3-ylcarboxamido)benzoic acid | intermediate compound 5 and 3-methoxyphenylboronic acid | 1 | 1.81 | 430 |
| 9 | 4-(3'-(Hydroxymethyl)-4-methylbiphenyl-3-ylcarboxamido)-3,5-dimethylbenzoic acid | intermediate compound 3a and 3-(hydroxymethyl)phenylboronic acid | 1 | 1.37 | 390 |
| 10 | 4-(5'-Chloro-2'-fluoro-4-methylbiphenyl-3-ylcarboxamido)-3,5-dimethylbenzoic acid | intermediate compound 3a and 5-chloro-2-fluorophenylboronic acid | 1 | 1.84 | 412 |
| 11 | 4-(2',5'-Difluoro-4-methylbiphenyl-3-ylcarboxamido)-3,5-dimethylbenzoic acid | intermediate compound 3a and 2,5-difluorophenylboronic acid | 1 | 1.72 | 396 |
| 12 | 4-(2'-fluoro-5'-methoxy-4-methylbiphenyl-3-ylcarboxamido)-3,5-dimethylbenzoic acid | intermediate compound 3a and 2-fluoro-5-methoxyphenylboronic acid | 1 | 1.72 | 408 |

| Example | Name | Starting Materials | UPLC method | $t_R$ (min) | m/z |
|---|---|---|---|---|---|
| 13 | 4-(3'-Carbamoyl-4-methylbiphenyl-3-ylcarboxamido)-3,5-dimethylbenzoic acid | intermediate compound 3a and 3-cyanophenylboronic acid | 1 | 1.25 | 403 |
| 14 | 4-(3',4-Dichlorobiphenyl-3-ylcarboxamido)-3,5-dimethylbenzoic acid | intermediate compound 3 and 3-chlorophenylboronic acid | 1 | 1.76 | 414 |
| 15 | 3,5-Dichloro-4-(3'-chloro-4-methylbiphenyl-3-ylcarboxamido)benzoic acid | intermediate compound 5 and 3-chlorophenylboronic acid | 1 | 1.91 | 434 |

Example 16: 3,5-Dichloro-4-(4-chloro-3'-(hydroxymethyl)biphenyl-3-ylcarboxamido)benzoic acid Following a similar procedure to that described in example 1 (section a), but using intermediate compound 4 and 3-(hydroxymethyl)phenylboronic acid instead of intermediate compound 3 and 3-methoxyphenylboronic acid, the desired compound was obtained.

LC-MS (method 1): $t_R$=1.45 min; m/z=449 (MH$^-$).

Following a similar procedure to that described in example 16, but using in each case the corresponding starting materials, the following compounds were obtained:

| Example | Name | Starting Materials | UPLC method | $t_R$ (min) | m/z |
|---|---|---|---|---|---|
| 17 | 3,5-Dichloro-4-(4-chloro-3'-methoxybiphenyl-3-ylcarboxamido)benzoic acid | intermediate compound 4 and 3-methoxyphenylboronic | 1 | 1.75 | 450 |
| 18 | 3,5-Dichloro-4-(4-chloro-3'-cyanobiphenyl-3-ylcarboxamido)benzoic acid | intermediate compound 4 and 3-cyanophenylboronic | 1 | 1.63 | 447 |
| 19 | 3,5-Dichloro-4-(3',4-dichlorobiphenyl-3-ylcarboxamido)benzoic acid | intermediate compound 4 and 3-chlorophenylboronic | 1 | 1.93 | 456 |

Example 20: 4-(3'-Chloro-4-methylbiphenyl-3-ylcarboxamido)-3,5-dimethylbenzoic acid a) 3'-Chloro-4-methylbiphenyl-3-carbonyl chloride Following a similar procedure to that described for intermediate compound 3 section a, but using intermediate compound 6 instead of 5-bromo-2-chlorobenzoic acid, the desired compound was obtained.

b) Ethyl 4-(3'-chloro-4-methylbiphenyl-3-ylcarboxamido)-3,5-dimethylbenzoate

Following a similar procedure to that described for intermediate compound 3 section b, but using the compound obtained in the previous section, instead of 5-bromo-2-chlorobenzoyl chloride, the desired compound was obtained.

LC-MS (method 1): $t_R$=2.91 min; m/z=422 (MH$^+$).

c) Title Compound

Following a similar procedure to that described in example 1 section b, but using the compound obtained in the previous section, the desired compound was obtained.

LC-MS (method 1): $t_R$=1.81 min; m/z=394 (MH$^+$).

Following a similar procedure to that described in example 20, but using in each case the corresponding starting materials, the following compounds were obtained:

| Example | Name | Starting Materials | UPLC method | $t_R$ (min) | m/z |
|---|---|---|---|---|---|
| 21 | 4-(3',4-Dichlorobiphenyl-3-ylcarboxamido)-3-methylbenzoic acid | intermediate compound 6a and methyl 4-amino-3-methylbenzoate | 1 | 1.80 | 400 |
| 22 | 3-Chloro-4-(3',4-dichlorobiphenyl-3-ylcarboxamido)-5-methylbenzoic acid | intermediate compound 6a and intermediate compound 1a | 1 | 1.88 | 434 |
| 23 | 4-(3-Chloro-6-(3-chlorophenyl)picolinamido)-3,5-dimethylbenzoic acid | intermediate compound 6b and intermediate compound 2 | 1 | 1.76 | 415 |
| 24[a] | 4-(2-Chloro-5-isobutoxybenzamido)-3,5-dimethylbenzoic acid | intermediate compound 2 and intermediate compound 8 | 1 | 1.72 | 376 |
| 25[a] | 3,5-Dichloro-4-(2-chloro-5-isobutoxybenzamido)benzoic acid | intermediate compound 1 and intermediate compound 8 | 1 | 1.84 | 416 |
| 26[a] | 3-Chloro-4-(2-chloro-5-isobutoxybenzamido)benzoic acid | intermediate compound 8 and methyl 4-amino-3-chlorobenzoate | 1 | 1.84 | 382 |
| 27[a] | 3-Chloro-4-(2-chloro-5-isobutoxybenzamido)-5-methylbenzoic acid | intermediate compound 1a and intermediate compound 8 | 1 | 1.79 | 396 |
| 28[a] | 4-(2-Chloro-5-isobutoxybenzamido)-3-methoxybenzoic acid | intermediate compound 1b and intermediate compound 8 | 1 | 1.81 | 378 |
| 29[a] | 4-(5-(Benzyloxy)-2-chlorobenzamido)-3,5-dichlorobenzoic acid | intermediate compound 1 and intermediate compound 8a | 1 | 1.86 | 415 |
| 30[a] | 3,5-Dichloro-4-(2-chloro-5-isopropoxybenzamido)benzoic acid | intermediate compound 1 and 2-chloro-5-isopropoxybenzoic acid | 1 | 1.68 | 403 |
| 31[a] | 3,5-Dichloro-4-(2-chloro-5-methoxybenzamido)benzoic acid | intermediate compound 1 and 2-chloro-5-methoxybenzoic acid | 1 | 1.42 | 375 |
| 32[a] | 3,5-Dichloro-4-(2-chloro-5-(cyclobutylmethoxy)benzamido)benzoic acid | intermediate compound 1 and 2-chloro-5-(cyclobutylmethoxy)benzoic acid[b] | 1 | 1.93 | 427 |
| 33[a] | 3,5-Dichloro-4-(2-chloro-5-ethoxybenzamido)benzoic acid | intermediate compound 1 and 2-chloro-5-ethoxybenzoic acid[c] | 1 | 1.57 | 387 |
| 34[a] | 3,5-Dichloro-4-(2-chloro-5-(neopentyloxy)benzamido)benzoic acid | intermediate compound 1 and 2-chloro-5-(neopentyloxy)benzoic acid[d] | 1 | 2.02 | 431 |
| 35[a] | 3,5-Dichloro-4-(2-chloro-5-(2,4-difluorobenzyloxy)benzamido)benzoic acid | intermediate compound 1 and 2-chloro-5-(2,4-difluorobenzyloxy)benzoic acid[e] | 1 | 1.88 | 485 |

-continued

| Example | Name | Starting Materials | UPLC method | $t_R$ (min) | m/z |
|---|---|---|---|---|---|
| 36[a] | 3,5-Dichloro-4-(2-chloro-5-(4-chloro-2-fluorobenzyloxy)benzamido)benzoic acid | intermediate compound 1 and 2-chloro-5-(4-chloro-2-fluoro-benzyloxy)benzoic acid[f] | 1 | 2.00 | 503 |
| 37 | 4-(2-Chloro-5-(2,4-difluorobenzyloxy)benzamido)-2,3,5,6-tetrafluorobenzoic acid | 2-chloro-5-(2,4-difluorobenzyloxy)benzoic acid[e] and methyl 4-amino-tetrafluorobenzoate | 1 | 1.86 | 489 |
| 38 | 3-(3'-Chloro-4-methylbiphenyl-3-ylcarboxamido)-4-methylbenzoic acid | intermediate compound 6 and methyl 3-amino-4-methylbenzoate | 1 | 1.79 | 379 |
| 39 | 3-(3',4-Dichlorobiphenyl-3-ylcarboxamido)-2-methylbenzoic acid | intermediate compound 6a and ethyl 3-amino-2-methylbenzoate | 1 | 1.66 | 400 |
| 40 | 3-(3',4-Dichlorobiphenyl-3-ylcarboxamido)-4-methylbenzoic acid | intermediate compound 6a and methyl 3-amino-4-methylbenzoate | 1 | 1.75 | 400 |
| 41 | 4-Chloro-3-(3',4-dichlorobiphenyl-3-ylcarboxamido)benzoic acid | intermediate compound 6a and ethyl 3-amino-4-chlorobenzoate | 1 | 1.86 | 420 |
| 42 | 3-(3-Chloro-6-(3-chlorophenyl)picolinamido)-4-methylbenzoic acid | intermediate compound 6b and methyl 3-amino-4-methylbenzoate | 1 | 1.78 | 401 |
| 43 | 3-(2-Chloro-5-(4-(trifluoromethyl)pyrimidin-2-yl)benzamido)-4-methylbenzoic acid | intermediate compound 6c and methyl 3-amino-4-methylbenzoate | 1 | 1.64 | 436 |
| 44 | 3-(2-Chloro-5-isobutoxybenzamido)-4-methylbenzoic acid | intermediate compound 8 and methyl 3-amino-4-methylbenzoate | 1 | 1.70 | 362 |
| 45 | 3-(3'-Chloro-4-methylbiphenyl-3-ylcarboxamido)-4-isopropylbenzoic acid | intermediate compound 6 and intermediate compound 10 | 1 | 1.93 | 407 |
| 46 | 3-(3',4-Dichlorobiphenyl-3-yl-carboxamido)-4-isopropylbenzoic acid | intermediate compound 6a and intermediate compound 10 | 1 | 1.91 | 428 |

[a] using $K_2CO_3$ and THF instead of DIPEA and $CH_2Cl_2$
[b] obtained as described in WO2009/056582
[c] obtained as described in WO2009/056582 but using iodoethane as alkylating agent
[d] obtained as described in WO2009/056582 but using neopentyl iodide as alkylating agent
[e] obtained as described in WO2009/056582 but using 1-(bromomethyl)-2,4-difluorobenzene as alkylating agent
[f] obtained as described in WO2009/056582 but using 1-(bromomethyl)-4-chloro-2-fluorobenzene as alkylating agent Example 47: 3,5-Dichloro-4-(3-chloro-6-(3-chlorophenyl)picolinamido)benzoic acid a) 3-Chloro-6-(3-chlorophenyl)picolinoyl chloride Following a similar procedure to that described in intermediate compound 3 section a, but using intermediate compound 6b instead of 5-bromo-2-chlorobenzoic acid, the desired compound was obtained b) Ethyl 3,5-dichloro-4-(3-chloro-6-(3-chlorophenyl)picolinamido)benzoate Following a similar procedure to that described in intermediate compound 5, but using the compound obtained in the previous section instead of 5-bromo-2-chlorobenzoyl chloride, the desired compound was obtained.

c) Title Compound

Following a similar procedure to that described in example 1 section b, but using the compound obtained in the previous section, instead ethyl 4-(4-chloro-3'-methoxybiphenyl-3-ylcarboxamido)-3,5-dimethylbenzoate, the desired compound was obtained.

LC-MS (method 1): $t_R$=1.83 min; m/z=457 (MH$^+$).

Following a similar procedure to that described in example 47, but using in the corresponding starting material, the following compound was obtained:

| Example | Name | Starting Materials | UPLC method | $t_R$ (min) | m/z |
|---|---|---|---|---|---|
| 48 | 3-Chloro-4-(3-chloro-6-(3-chlorophenyl)-picolinamido)-5-methylbenzoic acid | intermediate compound 6b and intermediate compound 1a | 1 | 1.84 | 437 |

Example 49: 3,5-Dichloro-4-(3-chloro-6-isobutoxypicolinamido)benzoic acid

To a solution of 2-methylpropan-1-ol (0.09 mL, 0.98 mmol) in DMF (5 mL) at 0° C., 55%, NaH dispersion in mineral oil (39 mg, 0.98 mmol) was added and the resulting suspension was stirred at room temperature for 2 h. Then a solution of the intermediate compound 7 (100 mg, 0.245 mmol) in DMF (3 mL) was added. The resulting mixture was stirred at room temperature overnight. The reaction mixture was quenched by adding saturated $NH_4Cl$ aqueous solution (5 mL) and extracted thrice with EtOAc. The combined organic phases were dried over $Na_2SO_4$ and concentrated to dryness. The crude residue was cromatographed on a silica gel flash system (Biotage SP1) using hexane/EtOAc mixtures of increasing polarity as eluent to afford 9.7 mg of the desired product (9.5% yield).

LC-MS (method 1): $t_R$=1.91 min; m/z=417 (MH$^+$).

Example 50: 3,5-Dichloro-4-(3-chloro-6-(cyclopropylmethylamino) picolinamido)benzoic acid A suspension of the intermediate compound 4a (60 mg, 0.158 mmol) in cyclopropylmethanamine (0.3 mL, 3.46 mmol) was heated in a Biotage microwave oven at 170° C. for 1 h. The solvent was evaporated to dryness and 12.1 mg of the title compound were obtained (yield 18.5%) after UPLC preparative purification).

LC-MS (method 1): $t_R$=1.63 min; m/z=414 (MH$^+$).

Following a similar procedure to that described in example 50, but using in each case the corresponding starting materials, the following compounds were obtained:

| Example | Name | Starting Materials | UPLC method | $t_R$ (min) | m/z |
|---|---|---|---|---|---|
| 51 | 3,5-Dichloro-4-(3-chloro-6-(cyclopentylamino)picolinamido)benzoic acid | cyclopentanamine | 1 | 1.77 | 428 |

-continued

| Example | Name | Starting Materials | UPLC method | $t_R$ (min) | m/z |
|---|---|---|---|---|---|
| 52 | 4-(6-(Benzylamino)-3-chloropicolinamido)-3,5-dichlorobenzoic acid | benzylamine | 1 | 1.67 | 450 |
| 53 | 3,5-Dichloro-4-(3-chloro-6-((2-methoxyethyl)(methyl)amino)-picolinamido)benzoic acid | 2-methoxy-N-methylethanamine | 1 | 1.54 | 432 |
| 54 | 4-(6-(Butyl(methyl)amino)-3-chloro-picolinamido)-3,5-dichlorobenzoic acid | N-methylbutan-1-amine | 1 | 1.93 | 430 |
| 55 | 3,5-Dichloro-4-(3-chloro-6-(diethylamino)picolinamido)benzoic acid | diethylamine | 1 | 1.81 | 416 |
| 56 | 3,5-Dichloro-4-(3-chloro-6-(propylamino)picolinamido)benzoic acid | propan-1-amine | 1 | 1.58 | 402 |
| 57 | 3,5-Dichloro-4-(3-chloro-6-(piperidin-1-yl)picolinamido)benzoic acid | piperidine | 1 | 1.84 | 428 |

Example 58: Sodium 3,5-dimethyl-4-(4-methyl-3'-(trifluoromethyl)biphenyl-3-ylcarboxamido)benzoate a) Ethyl 3,5-dimethyl-4-(4-methyl-3'-(trifluoromethyl)biphenyl-3-ylcarboxamido)benzoate Following a similar procedure to that described in example 1 section a, but using intermediate compound 3a and 3-trifluorophenylboronic acid instead of intermediate compound 3 and 3-methoxyphenylboronic, the desired compound was obtained.

b) Title Compound

To a solution of compound obtained above (113 mg, 0.248 mmol) in THF (3 mL), 2N NaOH aqueous solution (0.5 mL, 1 mmol) was added at room temperature. The mixture was stirred at 60° C. until TLC showed there was not starting material left. It was cooled and THF was removed in vacuo. The residue was dissolved in EtOAc, washed with water (×3) and brine, and dried with MgSO₄ to afford 45 mg of the desired compound (42% yield).

LC-MS (method 1): $t_R$=1.90 min, m/z=428

Following a similar procedure to that described in example 58, but using the corresponding starting materials, the following compound was obtained:

| Example | Name | Starting Materials | UPLC method | $t_R$ (min) | m/z |
|---|---|---|---|---|---|
| 59 | 4-(3'-Chloro-5'-methoxy-4-methyl-biphenyl-3-ylcarboxamido)-3,5-dimethyl-benzoic acid | intermediate compound 3a and 3-chloro-5-methoxyphenyl-boronic acid | 1 | 1.88 | 424 |

Example 60: Sodium 3,5-dichloro-4-(2-chloro-5-(4-(trifluoromethyl)pyrimidin-2-yl)benzamido)benzoate a) 2-Chloro-5-(4-(trifluoromethyl)pyrimidin-2-yl) benzoyl chloride Following a similar procedure to that described in intermediate compound 3 section a, but using intermediate compound 6c instead of 5-bromo-2-chlorobenzoic acid, the desired compound was obtained b) Title Compound To a solution of intermediate compound 1 (195 mg, 0.82 mmol) in DMF (4 mL) at −10° C., 55% NaH dispersion in mineral oil (108 mg, 2.47 mmol) was added and the resulting suspension was stirred at room temperature for 10 min. Then a solution of the compound obtained in the previous section (265 mg, 0.82 mmol) in DMF (2 mL) was added. The resulting mixture was stirred at room temperature overnight. Organic solvents were evaporated under reduced pressure. The reaction mixture was diluted by adding 1N NaOH aqueous solution (5 mL) and extracted thrice with EtOAc. The combined organic phases were dried over Na₂SO₄ and concentrated to dryness to afford 326 mg of the desired compound (77% yield).

LC-MS (method 1): $t_R$=1.77 min; m/z=492 (MH⁺).

Example 61: 3,5-Dichloro-4-(5-(cyclohexylmethyl)-2-methylbenzamido)benzoic acid a) 5-(Cyclohexylmethyl)-2-methylbenzoyl chloride Following a similar procedure to that described in intermediate compound 3 section a, but using intermediate compound 9 instead of 5-bromo-2-chlorobenzoic acid, the desired compound was obtained b) Title Compound To a solution of intermediate compound 1 (260 mg, 1.11 mmol) in DMF (5 mL) at −10° C., 55% NaH dispersion in mineral oil (145 mg, 2.47 mmol) was added and the resulting suspension was stirred at room temperature for 10 min. Then a solution of the compound obtained in the previous section (258 mg, 1.11 mmol) in DMF was added. The resulting mixture was stirred at room temperature overnight. The reaction mixture was quenched by adding 1N HCl aqueous solution (5 mL) and extracted thrice with EtOAc. The combined organic phases were dried over Na₂SO₄ and concentrated to dryness. The crude residue was cromatographed on a silica gel flash system (Biotage SP1) using hexane/EtOAC mixtures of increasing polarity as eluent to afford 497 mg of the desired product (100% yield).

LC-MS (method 1): $t_R$=2.20 min; m/z=420 (MH⁺).

Following a similar procedure to that described in example 61, but using in each case the corresponding starting materials, the following compounds were obtained:

| Example | Name | Starting Materials | UPLC method | $t_R$ (min) | m/z |
|---|---|---|---|---|---|
| 62 | 4-(5-Benzyl-2-chlorobenzamido)-3,5-dichlorobenzoic acid | intermediate compound 9a | 1 | 1.84 | 434 |

| Example | Name | Starting Materials | UPLC method | $t_R$ (min) | m/z |
|---|---|---|---|---|---|
| 63 | 3,5-Dichloro-4-(2-chloro-5-isobutyl-benzamido)-benzoic acid | intermediate compound 9b | 1 | 1.86 | 402 |

Example 64: 4-(2-Chloro-5-isobutoxy-N-methylbenzamido)-3,5-dimethylbenzoic acid To a solution of example 24 (150 mg, 0.4 mmol) and iodomethane (0.1 mL, 1.6 mmol) in THF (4 mL) at 0° C., 55% NaH dispersion in mineral oil (52 mg, 1.2 mmol) was added and the resulting suspension was stirred at room temperature overnight. Organic solvents were evaporated under reduced pressure and the pH of the solution was adjusted to 2 by adding 10% HCl aqueous solution. The resulting mixture was filtered and the collected solids were washed with water and dried overnight in the oven to afford 127 mg of the desired product (82% yield).

LC-MS (method 1): $t_R$=1.83 min; m/z=390 (MH$^+$).

Following a similar procedure to that described in example 64, but using in each case the corresponding starting materials, the following compounds were obtained:

| Example | Name | Starting Materials | UPLC method | $t_R$ (min) | m/z |
|---|---|---|---|---|---|
| 65 | 3,5-Dichloro-4-(2-chloro-5-isobutoxy-N-methylbenzamido)benzoic acid | example 25 and iodomethane | 1 | 1.99 | 430 |
| 66 | 3,5-Dichloro-4-(2-chloro-5-isobutoxy-N-ethylbenzamido)benzoic acid | example 25 and iodoethane | 1 | 2.06 | 444 |
| 67 | 3,5-Dichloro-4-(2-chloro-5-isobutoxy-N-isobutylbenzamido)benzoic acid | example 25 and 1-iodo-2-methylpropane | 1 | 2.00 | 472 |
| 68 | 3,5-Dichloro-4-(2-chloro-5-isobutoxy-N-propylbenzamido)benzoic acid | example 25 and 1-iodopropane | 1 | 1.90 | 458 |
| 69 | 3,5-Dichloro-4-(2-chloro-5-(2,4-difluorobenzyloxy)-N-ethylbenzamido)benzoic acid | example 35 and iodoethane | 1 | 2.05 | 513 |
| 70 | 3,5-Dichloro-4-(2-chloro-5-(4-chloro-2-fluorobenzyloxy)-N-ethylbenzamido)benzoic acid | example 36 and iodoethane | 1 | 1.97 | 531 |

Example 71: Sodium 3-(5-(benzyloxy)-2-chlorobenzamido)-4-methylbenzoate a) Ethyl 3-(5-(benzyloxy)-2-chlorobenzamido)-4-methylbenzoate

Following a similar procedure to that described in example 20 section b, but using intermediate compound 8a and methyl 3-amino-4-methylbenzoate as starting materials, the desired compound was obtained.

b) Title Compound

To a solution of compound obtained above (15 mg, 0.037 mmol) in MeOH (1 mL), 1N NaOH aqueous solution (0.055 mL, 0.055 mmol) was added at room temperature. The mixture was stirred at 70° C. until TLC showed there was not starting material left. It was cooled and THF was removed in vacuo to afford 15 mg of the desired compound (100% yield).

LC-MS (method 1): tR=1.71 min, m/z=396

Examples of Biological Activity

In the following examples the biological activity of compounds of formula (I) towards EP4 receptors is shown.

Test 1: Human EP4 Receptor Radioligand Binding Assay

To investigate binding properties of EP4 receptor ligands to human EP4 receptor, transfected HEK-293 cell membranes and [3H]-PGE2 (Perkin Elmer) were used. In 96-well plates the assay was carried out with a total reaction volume of 250 µl, containing 25 µl of membrane suspension (30 µg protein/well), 25 µl of [3H]-PGE2 (1 nM) in either absence or presence of 25 µl of either buffer or PGE2 (10 µM) for total and non-specific binding, respectively. Binding buffer contained 25 mM MES, 10 mM MgCl$_2$ and 1 mM EDTA at pH 6.0. Plates were incubated at 25° C. for 120 minutes. After the incubation period, 200 µl of incubate were transferred to MultiScreen HTS, FB plates (Millipore), filtered and plates were washed 6 times with ice-cold 10 mM MES, 0.01% BSA at pH 6.0. Filters were dried and counted in a MicroBeta scintillation counter (Perkin-Elmer) using EcoScint liquid scintillation cocktail.

Percentage inhibition was calculated relating compounds activity to the 0% inhibition of the wells incubated with 1 nM [3H]-PGE2 alone (total binding) and 100% inhibition of the wells incubated with 1 nM [3H]-PGE2 plus 10 µM PGE2 (non-specific binding).

Test 2: Measurement of cAMP Responses by Homogeneous Time Resolved Fluorescence cAMP measurements on HEK-293 cells that stably expressed human EP4 receptors were performed by using a system based on Homogeneous Time Resolved Fluorescence (HTRF). This technology allows the direct measurement of cAMP in living cells. The principle of this assay is based on competition between cAMP produced by cells and cAMP-d2 conjugate for the binding with monoclonal anti-cAMP-cryptate conjugate. The HTRF cAMP kit from Cis-Bio was used according to the manufacturer's directions. The experimental procedure was performed as stated below.

Suspended cells (30,000 cells per well) were added to 96-well culture plates in 30 µl of Optimem supplemented with 500 µM IBMX. Compounds were then added in 10 µl of stimulation buffer and incubated at 25° C. for 30 minutes followed by 10 µl of PGE2 to a final concentration of 1 nM. After 30 minutes at 25° C., the reaction was stopped lysing the cells with a mixture of 25 µl of cryptate and 25 µl of cAMP-d2 prepared in the lysis buffer supplied by the manufacturer. Plates were incubated for an additional hour at room temperature and read at 665 nm/620 nm using an UltraEvolution Plate reader (Tecan).

Antagonist percentage inhibition was calculated relating compounds activity to the 0% inhibition of the wells incubated with 1 nM PGE2 alone and 100% inhibition of the wells incubated with 1 nM PGE2 plus 1 µM of the reference antagonist.

| Example | Results of Test 1* | Results of Test 2** |
|---|---|---|
| 1 | # | $ |
| 2 | # | $ |
| 3 | # | $ |
| 4 | # | $ |
| 5 | # | $ |
| 6 | # | $ |
| 7 | # | $ |
| 8 | # | $ |
| 9 | # | $ |
| 10 | # | $ |
| 11 | # | $ |
| 12 | # | $ |
| 13 | # | $ |
| 14 | # | $ |
| 15 | # | $ |
| 16 | # | $ |
| 17 | # | $ |
| 18 | # | $ |
| 19 | # | $ |
| 20 | # | $ |
| 21 | # | $ |
| 22 | # | $ |
| 23 | # | $ |
| 24 | # | $ |
| 25 | # | $ |
| 26 | # | |
| 27 | # | |
| 28 | # | |
| 29 | # | |
| 30 | # | |
| 31 | # | |
| 32 | # | |
| 33 | # | |
| 34 | # | |
| 35 | # | $ |
| 36 | # | $ |
| 37 | ## | |
| 38 | # | $ |
| 39 | # | |
| 40 | # | |
| 41 | # | |
| 42 | # | $ |
| 43 | # | |
| 44 | # | |
| 45 | # | $ |
| 46 | # | $ |
| 47 | # | $ |
| 48 | # | $ |
| 49 | # | |
| 50 | # | |
| 51 | # | |
| 53 | # | |
| 54 | # | |
| 55 | # | |
| 56 | # | |
| 57 | # | $ |
| 58 | # | $ |
| 59 | # | $ |
| 60 | # | $ |
| 61 | # | |
| 62 | # | |
| 63 | # | |
| 66 | # | |
| 67 | # | |
| 69 | # | |
| 70 | # | |
| 71 | # | |

*Binding assay (Test 1) at 10 µM # % inh >75, ## 45 < % inh <75;
**Functional assay (Test 2) at 10 µM $ % inh >75.

REFERENCES

Coleman, R. A., Prostanoid Receptors. IUPHAR compendium of receptor characterization and classification, $2^{nd}$ edition, 338-353, 2000.

Chen Q, Muramoto K, Masaaki N, Ding Y, Yang H, Mackey M, Li W, Inoue Y, Ackermann K, Shirota H, Matsumoto I, Spyvee M, Schiller S, Sumida T, Gusovsky F, Lamphier M. A novel antagonist of the prostaglandin E(2) EP(4) receptor inhibits Th1 differentiation and Th17 expansion and is orally active in arthritis models Br J Pharmacol. 2010 May; 160(2):292-310.

Cherukuri D P, Chen B O, Goulet A-C, Young R N, Han Y, Heimark R L, Regan J W, Meuillet E, Nelson M A. The EP4 receptor antagonist, L-161,982, blocks prostaglandin E2-induced signal transduction and cell proliferation in HCA-7 colon cancer cells. Experimental Cell Research 313 (2007) 2969-2979.

Yao-Chi Chuang, Pradeep Tyagi, Chao-Cheng Huang, Michael B. Chancellor and Naoki Yoshimura. Mechanisms and urodynamic effects of a potent and selective EP4 receptor antagonist, MF191, on cyclophosphamide and prostaglandin E 2-induced bladder overactivity in rats. BJU International' 110, 1558-1564 (2012)

Davis R J, Murdoch C E, Ali M, Purbrick S, Ravid R, Baxter G S et al. (2004). EP4 prostanoid receptor-mediated vasodilatation of human middle cerebral arteries. Br J Pharmacol 141: 580-585.

Dirig D M, Yaksh T L. (1999) In vitro prostanoid release from spinal cord following peripheral inflammation: effects of substance P, NMDA and capsaicin. Br J Pharmacol. 126(6):1333-40.

T. W. Greene and P. G. M. Wuts "Protective groups in organic synthesis" (John Wiley & sons 10 1999)

Folkman J. Angiogenesis: an organizing principle for drug discovery? Nat Rev Drug Discov. 2007 April; 6(4):273-86.

Guay J., Bateman, K., Gordon R., Mancini J., Riendeau D. (2004) Carrageenan-induced paw edema in rat elicits a predominant prostaglandin E2 (PGE2) response in the central nervous system associated with the induction of microsomal PGE2 synthase-1 J. Biol Chem 2004.279, 24866-24872.

Heidenreich R, ROcken M, Ghoreschi K. Angiogenesis drives psoriasis pathogenesis. Int J Exp Pathol. 2009 June; 90(3):232-48.

Jones R L, Giembycz M A and Woodward D F. Prostanoid receptor antagonists: development strategies and therapeutic applications. British Journal of Pharmacology (2009) 158 104-145

Lin C R, Amaya F, Barrett L, Wang H, Takada J, Samad T A, Woolf C J (2006) Prostaglandin E2 receptor EP4 contributes to inflammatory pain hypersensitivity. J Pharmacol Exp Ther. 319(3):1096-103.

Lee J, Banu S K, Rodriguez R, Starzinski-Powitz A, Arosh J A. Selective blockade of prostaglandin E(2) receptor EP2 and EP4 signaling inhibits proliferation of human endometriotic epithelial cells and stromal cells through distinct cell cycle arrest. Fertil Steril. 2010 Mar. 5.

Ma W, Eisenach J C. (2003) Four PGE2 EP receptors are up-regulated in injured nerve following partial sciatic nerve ligation. Exp Neurol. 183(2):581-92.

Maher, Sarah A.; Belvisi, Maria G. Prostanoids and the Cough Reflex. Lung 2010; 188 (Suppl. 1): 9-12.

McCoy, Jennifer M; Wicks, Joan R.; and Audoly, Laurent P. The role of prostaglandin E2 receptors in the pathogenesis of rheumatoid arthritis. J. Clin. Invest. 110:651-658 (2002).

Maubach K A, Clark D E, Fenton G, Lockey P M, Clark K L, Oxford A W et al. (2009). BCG20-1531, a novel, potent and selective prostanboid EP4 receptor antagonist; a putative new treatment for migraine headache. Br J Pharmacol 156: 316-327.

Narumiya S., Sugimoto Y., Ushikubi F. (1999) Protanoid receptors: structures, properties, and functions. Physiol Rev. 79 (1999) 1193-1226.

Oka T, Hosoi M, Oka K, Hori T. (1997) Biphasic alteration in the trigeminal nociceptive neuronal responses after intracerebroventricular injection of prostaglandin E2 in rats. Brain Res. 749(2):354-7. Erratum in: Brain Res 757(2):299.

Samad T A, Sapirstein A, Woolf C J. (2002) Prostanoids and pain: unraveling mechanisms and revealing therapeutic targets. Trends Mol Med. 2002 August; 8(8):390-6.

Syriatowicz J P, Hu D, Walker J S, Tracey D J. (1999) Hyperalgesia due to nerve injury: role of prostaglandins. Neuroscience. 94(2):587-94.

Takayama K, Sukhova G K, Chin M T, et al. A novel prostaglandin E receptor 4 associated protein participates in anti-inflammatory signaling. Circ Res. 2006; 98:499-504.

Wei, Li-Li; Shen, Yue-Di; Zhang, Ying-Chun; Hu, Xing-Yue; Lu, Pei-Ling; Wang, Li; Chen, Wei. Roles of the prostaglandin E2 receptors EP subtypes in Alzheimer's disease. Neurosci Bull 2010; 26 (1): 77-84.

Wu W K, Sung J J, Lee C W, Yu J, Cho C H. Cyclooxygenase-2 in tumorigenesis of gastrointestinal cancers: an update on the molecular mechanisms. Cancer Lett. 2010 Sep. 1; 295(1):716.

Yao C., Daiji Sakata, Yoshiyasu Esaki, Youxian Li, Toshiyuki Matsuoka, Kenji Kuroiwa, Yukihiko Sugimoto, Shuh Narumiya. Prostaglandin E2-EP4 signaling promotes immune inflammation through TH1 cell differentiation and TH17 cell expansion. Nature Medicine Vol 15, no 6 (2009) 633-40.

Yao C, Hirata T, Soontrapa K, Ma X, Takemori H, Narumiya S. Prostaglandin E2 promotes Th1 differentiation via synergistic amplification of IL-12 signalling by cAMP and PI3-kinase. Nat Commun. 2013; 4:1685.

Zimecki, M. Potential therapeutic interventions via EP2/EP4 prostaglandin receptors., 2012; 66; 287-294

The invention claimed is:

1. A compound of general formula I:

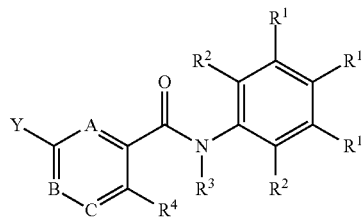

(I)

wherein:
each $R^1$ may be a —COOH; a H; a halogen; a —SO$_2$—NH—C(=O)—R'; or a —C(=O)NH—SO$_2$—R'; with the proviso that only one of them must always represent a —COOH; or SO$_2$—NH—C(=O)—R' or C(=O)NH—SO$_2$—R', each $R^2$ is independently selected from the group consisting of H; a halogen; $C_{1-6}$-alkyl; or —O—$C_{1-6}$-alkyl, with the proviso that at least one $R^2$ must be different from H;

$R^3$ is selected from H; or a $C_{1-6}$-alkyl;

$R^4$ is a halogen or a $C_{1-6}$-alkyl;

A, B and C represents a $CR^a$;

Y is a —$NR^5R^6$; an —$OR^7$; a phenyl, optionally substituted by at least one $R^b$; a benzyl optionally substituted by at least one $R^b$; a 5- or 6-membered non-aromatic heterocyclic ring, optionally substituted by at least one $R^b$, containing at least one heteroatom selected from N, O or S; a $C_{1-4}$-alkylene-$C_{3-6}$-cycloalkyl; or a $C_{2-6}$-alkyl;

$R^5$ and $R^6$ are independently selected from H; a $C_{1-6}$-alkyl; a benzyl; a $C_{3-6}$cycloalkyl; —$C_{1-4}$-alkylene-$C_{3-6}$cycloalkyl; or —$C_{1-4}$-alkylene-$C_{1-6}$-alkyloxy;

$R^7$ is a H, a $C_{1-6}$-alkyl, a benzyl optionally substituted by at least one $R^c$; or a —$C_{1-4}$-alkylene-$C_{3-6}$cycloalkyl;

R' is independently selected from a hydrogen; $C_{1-6}$-alkyl; an optionally substituted phenyl; or —N(CH$_3$)$_2$;

$R^a$ is a H or a $C_{1-6}$-alkyl;

each $R^b$ is independently a H; a $C_{1-6}$-alkyl; a halogen; a —CN; a trihalo-$C_{1-6}$-alkyl; a —$CONR^8R^9$; an —$OR^{10}$ or —$C_{1-4}$-alkylene-$OR^{11}$;

each $R^c$ is independently a H; a $C_{1-6}$-alkyl; or a halogen;

$R^8$ and $R^9$ are independently selected from H; or a $C_{1-6}$-alkyl;

$R^{10}$ and $R^{11}$ are independently selected from H; or a $C_{1-6}$-alkyl;

with the proviso that when $R^1$ is COOH in meta position and $R^2$ is either methyl or Cl or when $R^1$ is COOH in para position and $R^2$ is methyl, $R^7$ is not methyl and $R^4$ is not Br, and the salts and solvates thereof.

2. A compound according to claim 1 wherein one $R^1$ substituent is —COOH and the other two $R^1$ substituents are hydrogen.

3. A compound according to claim 1 where each $R^2$ is independently selected from H, methyl or Cl with the proviso that at least one $R^2$ is different from H.

4. A compound according to claim 1 where each $R^4$ is independently selected from methyl or Cl.

5. A compound according to claim 1 where Y is a —$NR^5R^6$; an —$OR^7$ or one of the following groups:

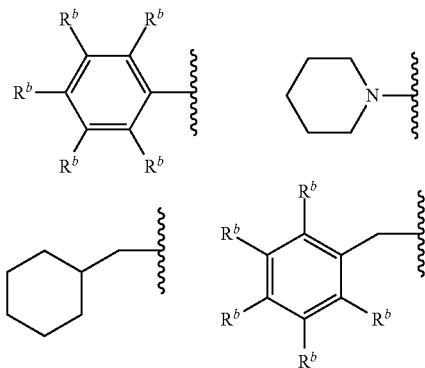

where $R^5$, $R^6$, $R^7$ and $R^b$ have the same meanings as in claim 1.

6. A compound according to claim 1 having general formula (Ia):

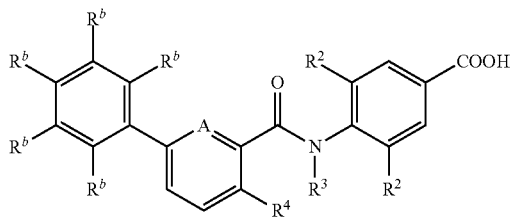

(Ia)

where $R^2$, $R^3$, $R^4$, $R^b$ and A have the same meaning as in claim 1.

7. A compound according to claim 1 having general formula (Ib):

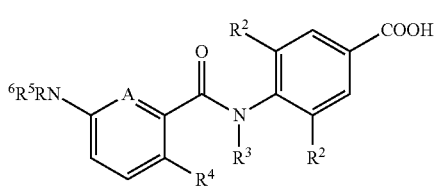

(Ib)

where $R^2$, $R^3$, $R^4$, $R^5$, $R^6$ and A have the same meaning as in claim 1.

8. A compound according to claim 1 having general formula (Ic):

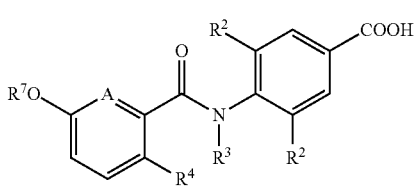

(Ic)

where $R^2$, $R^3$, $R^4$, $R^7$ and A have the same meaning as in claim 1.

9. The compound according to claim 1 selected from:
- 4-(4-Chloro-3'-methoxybiphenyl-3-ylcarboxamido)-3,5-dimethylbenzoic acid;
- 4-(4-Chloro-3'-(hydroxymethyl)biphenyl-3-ylcarboxamido)-3,5-dimethylbenzoic acid;
- 4-(3'-Methoxy-4-methylbiphenyl-3-ylcarboxamido)-3,5-dimethylbenzoic acid;
- 4-(3'-Fluoro-4-methylbiphenyl-3-ylcarboxamido)-3,5-dimethylbenzoic acid;
- 4-(3'-Cyano-4-methylbiphenyl-3-ylcarboxamido)-3,5-dimethylbenzoic acid;
- 3,5-Dichloro-4-(3'-(hydroxymethyl)-4-methylbiphenyl-3-ylcarboxamido)benzoic acid;
- 3,5-Dichloro-4-(3'-cyano-4-methylbiphenyl-3-ylcarboxamido)benzoic acid;
- 3,5-Dichloro-4-(3'-methoxy-4-methylbiphenyl-3-ylcarboxamido)benzoic acid;
- 4-(3'-(Hydroxymethyl)-4-methylbiphenyl-3-ylcarboxamido)-3,5-dimethylbenzoic acid;
- 4-(5'-Chloro-2'-fluoro-4-methylbiphenyl-3-ylcarboxamido)-3,5-dimethylbenzoic acid;
- 4-(2',5'-Difluoro-4-methylbiphenyl-3-ylcarboxamido)-3,5-dimethylbenzoic acid;
- 4-(2'-fluoro-5'-methoxy-4-methylbiphenyl-3-ylcarboxamido)-3,5-dimethylbenzoic acid;
- 4-(3'-Carbamoyl-4-methylbiphenyl-3-ylcarboxamido)-3,5-dimethylbenzoic acid;
- 4-(3',4-Dichlorobiphenyl-3-ylcarboxamido)-3,5-dimethylbenzoic acid;
- 3,5-Dichloro-4-(3'-chloro-4-methylbiphenyl-3-ylcarboxamido)benzoic acid;
- 3,5-Dichloro-4-(4-chloro-3'-(hydroxymethyl)biphenyl-3-ylcarboxamido)benzoic acid;
- 3,5-Dichloro-4-(4-chloro-3'-methoxybiphenyl-3-ylcarboxamido)benzoic acid;
- 3,5-Dichloro-4-(4-chloro-3'-cyanobiphenyl-3-ylcarboxamido)benzoic acid;
- 3,5-Dichloro-4-(3',4-dichlorobiphenyl-3-ylcarboxamido)benzoic acid;
- 4-(3'-Chloro-4-methylbiphenyl-3-ylcarboxamido)-3,5-dimethylbenzoic acid;
- 4-(3',4-Dichlorobiphenyl-3-ylcarboxamido)-3-methylbenzoic acid;
- 3-Chloro-4-(3',4-dichlorobiphenyl-3-ylcarboxamido)-5-methylbenzoic acid;
- 4-(2-Chloro-5-isobutoxybenzamido)-3,5-dimethylbenzoic acid;
- 3,5-Dichloro-4-(2-chloro-5-isobutoxybenzamido)benzoic acid;
- 3-Chloro-4-(2-chloro-5-isobutoxybenzamido)benzoic acid;
- 3-Chloro-4-(2-chloro-5-isobutoxybenzamido)-5-methylbenzoic acid;
- 4-(2-Chloro-5-isobutoxybenzamido)-3-methoxybenzoic acid;
- 4-(5-(Benzyloxy)-2-chlorobenzamido)-3,5-dichlorobenzoic acid;
- 3,5-Dichloro-4-(2-chloro-5-isopropoxybenzamido)benzoic acid;
- 3,5-Dichloro-4-(2-chloro-5-methoxybenzamido)benzoic acid;
- 3,5-Dichloro-4-(2-chloro-5-(cyclobutylmethoxy)benzamido)benzoic acid;
- 3,5-Dichloro-4-(2-chloro-5-ethoxybenzamido)benzoic acid;
- 3,5-Dichloro-4-(2-chloro-5-(neopentyloxy)benzamido)benzoic acid;
- 3,5-Dichloro-4-(2-chloro-5-(2,4-difluorobenzyloxy)benzamido)benzoic acid;
- 3,5-Dichloro-4-(2-chloro-5-(4-chloro-2-fluorobenzyloxy)benzamido)benzoic acid;
- 4-(2-Chloro-5-(2,4-difluorobenzyloxy)benzamido)-2,3,5,6-tetrafluorobenzoic acid;
- 3-(3'-Chloro-4-methylbiphenyl-3-ylcarboxamido)-4-methylbenzoic acid;
- 3-(3',4-Dichlorobiphenyl-3-ylcarboxamido)-2-methylbenzoic acid;
- 3-(3',4-Dichlorobiphenyl-3-ylcarboxamido)-4-methylbenzoic acid;
- 4-Chloro-3-(3',4-dichlorobiphenyl-3-ylcarboxamido)benzoic acid;

3-(2-Chloro-5-isobutoxybenzamido)-4-methylbenzoic acid;
3-(3'-Chloro-4-methylbiphenyl-3-ylcarboxamido)-4-isopropylbenzoic acid;
a 3-(3',4-Dichlorobiphenyl-3-ylcarboxamido)-4-isopropylbenzoic acid;
Sodium 3,5-dimethyl-4-(4-methyl-3'-(trifluoromethyl)biphenyl-3-ylcarboxamido)benzoate;
a 4-(3'-Chloro-5'-methoxy-4-methylbiphenyl-3-ylcarboxamido)-3,5-dimethylbenzoic acid;
3,5-Dichloro-4-(5-(cyclohexylmethyl)-2-methylbenzamido)benzoic acid;
4-(5-Benzyl-2-chlorobenzamido)-3,5-dichlorobenzoic acid;
a 3,5-Dichloro-4-(2-chloro-5-isobutylbenzamido)benzoic acid;
3,5-Dichloro-4-(2-chloro-5-isobutoxy-N-methylbenzamido)benzoic acid;
3,5-Dichloro-4-(2-chloro-5-isobutoxy-N-ethylbenzamido)benzoic acid;
3,5-Dichloro-4-(2-chloro-5-isobutoxy-N-isobutylbenzamido)benzoic acid;
3,5-Dichloro-4-(2-chloro-5-isobutoxy-N-propylbenzamido)benzoic acid;
3,5-Dichloro-4-(2-chloro-5-(2,4-difluorobenzyloxy)-N-ethylbenzamido)benzoic acid;
3,5-Dichloro-4-(2-chloro-5-(4-chloro-2-fluorobenzyloxy)-N-ethylbenzamido)benzoic acid;
Sodium 3-(5-(benzyloxy)-2-chlorobenzamido)-4-methylbenzoate;
and the salts and solvates thereof.

10. A compound according to claim 1 for use as a medicament.

11. A compound according to claim 1 for use in the treatment and/or prophylaxis of diseases or disorders mediated by the EP4 receptor.

12. A compound for use according to claim 11 where the disease or disorders comprises inflammatory related pain including low back and neck pain, skeletal pain, post-partum pain, toothache, sprains and straits, myositis, neuralgia, synovitis, arthritis, including rheumatoid arthritis, degenerative joint diseases, gout and ankylosing spondylitis, bursitis, burns including radiation and corrosive chemical injuries and sunburns; postoperative pain; neuropathic pain; visceral pain; tension headache; cluster headaches; migraine; motility-related disorders including gastrointestinal disorders, urinary incontinence and other urinary tract diseases; dysmenorrhea; preterm labour; diabetic retinopathy; tumour angiogenesis; cancer; metastatic tumour growth; neurodegenerative diseases including senile dementia, Alzheimer's disease, Pick's disease, Huntington's chorea, Parkinson's disease, Creutzfeldt-Jakob disease, or amyotrophic lateral sclerosis; neuroprotection/stroke; glaucoma; osteoporosis; bone fractures; Paget's disease; hyperthermia including different types of fever as rheumatic fever; symptoms associated with influenza or other viral infections; gastrointestinal disorders related with chemotherapy or irritable bowel syndrome; gastrointestinal bleeding; coagulation disorders including anaemia, hypoprothrombinemia, haemophilia or other bleeding problems; kidney diseases including nephritis, particularly mesangial proliferative glomerulonephritis and nephritic syndrome; thrombosis and occlusive vascular diseases; inflammatory diseases including the treatment of skin conditions such as, bums, eczema, dermatitis, psoriasis; ophthalmic diseases including glaucoma, retinitis, retinopathies, uveitis and of acute injury to the eye tissue such as conjunctivitis; lung disorders including asthma, bronchitis, emphysema, allergic rhinitis, respiratory distress syndrome pigeon fancier's disease, farmer's lung, CORD; gastrointestinal tract disorders including aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease; organ tnasplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythemato sus, polymyositis, tendinitis, bursitis, and Sjogren's syndrome; bone diseases characterized by abnormal bone metabolism or resorption such as osteoporosis, especially postmenopausal osteoporosis, hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis, especially urolithiasis, solid carcinoma, gout and ankylosing spondylitis, tendinitis and bursitis; immune diseases such as multiple sclerosis, rheumatoid arthritis, inflammatory bowel diseases and allergic skin disorders; contact hypersensitivity, cough and endometriosis.

13. A compound according to claim 11 where the disease or disorders comprises inflammatory related pain including low back and neck pain, skeletal pain, post-partum pain, toothache, sprains and straits, myositis, neuralgia, synovitis, arthritis, including rheumatoid arthritis, degenerative joint diseases, gout and ankylosing spondylitis, bursitis, burns including radiation and corrosive chemical injuries and sunburns; postoperative pain; neuropathic pain; visceral pain; tension headache; cluster headaches; migraine; urinary incontinence and other urinary tract diseases; inflammatory diseases including the treatment of skin conditions such as sunburn, bums, eczema, dermatitis, psoriasis; ophthalmic diseases such as glaucoma, retinitis, retinopathies, uveitis and of acute injury to the eye tissue such as conjunctivitis; lung disorders including asthma, bronchitis, emphysema, allergic rhinitis, respiratory distress syndrome pigeon fancier's disease, farmer's lung, CORD; gastrointestinal tract disorders including aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease; organ tnasplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythemato sus, polymyositis, tendinitis, bursitis, and Sjogren's syndrome; bone diseases characterized by abnormal bone metabolism or resorption such as osteoporosis, especially postmenopausal osteoporosis, hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis, especially urolithiasis, solid carcinoma, gout and ankylosing spondylitis, tendinitis and bursitis; immune diseases such as multiple sclerosis, rheumatoid arthritis, inflammatory bowel diseases and allergic skin disorders; contact hypersensitivity, cough and endometriosis.

14. Pharmaceutical composition comprising at least one compound according to claim 1 and at least one pharmaceutically acceptable carrier, additive, adjuvant or vehicle.

15. A compound according to claim 1 wherein one $R^1$ substituent is —COOH and the other two $R^1$ substituents are hydrogen.

16. A compound according to claim 1 where Y is a —$NR^5R^6$; an —$OR^7$ or one of the following groups:

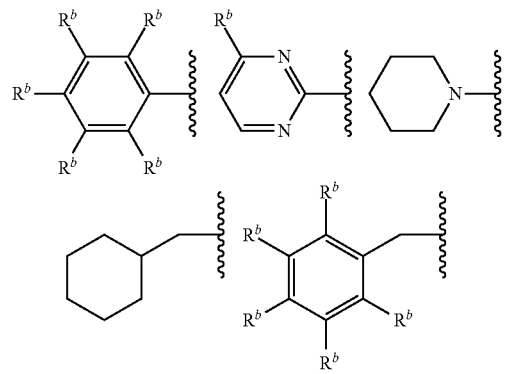

where $R^5$, $R^6$, $R^7$ and $R^b$ have the same meanings as in claim 1.

17. A compound according to claim 1 having general formula (Ia):

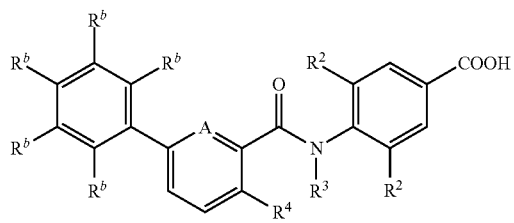

where $R^2$, $R^3$, $R^4$, $R^b$ and A have the same meaning as in claim 1.

18. A compound according to claim 1 having general formula (Ib):

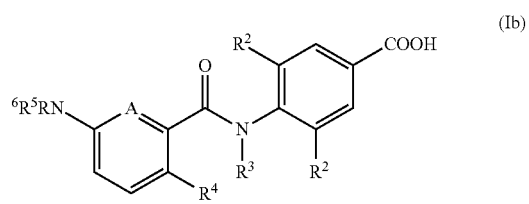

where $R^2$, $R^3$, $R^4$, $R^5$, $R^6$ and A have the same meaning as in claim 1.

* * * * *